United States Patent [19]
Knight et al.

[11] Patent Number: 5,370,868
[45] Date of Patent: Dec. 6, 1994

[54] THERAPEUTIC USE OF VITALETHEINE MODULATORS IN NEOPLASIA

[75] Inventors: Galen D. Knight; Terence J. Scallen, both of Albuquerque, N. Mex.

[73] Assignee: University of New Mexico, Albuquerque, N. Mex.

[21] Appl. No.: 928,725

[22] Filed: Aug. 13, 1992

Related U.S. Application Data

[63] Continuation-in-part of Ser. No. 549,440, Jul. 6, 1990, abandoned.

[51] Int. Cl.[5] .................. A61K 31/785; A61K 31/795; A61K 31/16
[52] U.S. Cl. .............................. 424/78.08; 424/78.37; 514/563
[58] Field of Search ................. 424/78.08, 78.35, 78.37

[56] References Cited

PUBLICATIONS

*Tetrahedron Letters* 22:4365–4368, 1981, "Tricyclic Orthoacetamides and Orthopropionamides".
*J. Am. Chem. Soc.* 86:1202–1206, 1967, "On the Synthesis of Cystein Peptides".
*Nauchnoizskd. Inst. Radiobiol. Radiats. Khigy.* 5, 57–62, 1975, "Synthesis of S-(omega-Carboxamidinoalkyl-)-Isothiocarbamides".
*Merck Index* 1974, #221.

*Primary Examiner*—Edward J. Webman
*Attorney, Agent, or Firm*—Hoffman, Wasson & Gitler

[57] ABSTRACT

A method for treating neoplasia using sulfur-containing derivatives of carboxy-amino-amides, comprising vitaletheine and vitalethine and related compounds, is provided.

2 Claims, 23 Drawing Sheets

THERAPEUTIC USE OF VITALETHEINE MODULATORS IN NEOPLASIA

This is a continuation-in-part of copending application Ser. No. 07/549,440 filed on Jul. 6, 1990, abandoned.

BACKGROUND OF THE INVENTION

This invention was made in the performance of work under a grant from the National Institute of Health #HL 16,796; AN 10,628; and BRSG S07RR-05583-25 and the U.S. Government has certain rights therein.

1. Field of the Invention

The invention provides a novel method using a group of compounds to modulate biological activities comprising sulfur-containing hydrocarbon derivatives of carboxy-amino-amides such as vitaletheine, [N-(2-mercapto-ethane)-3-carboxyamino-propanamide], also designated as N-[3-(2-mercapto-ethanamino)-3-oxo-3,1-propanediyl]-carbamic acid, herein referred to as "vitaletheine modulators". The compounds are characterized by a pronounced biological activity, and are useful, inter alia, for reestablishing the normal phenotypic expression of neoplastic cells in vivo and in vitro, and for stimulating immunological surveillance for neoplastic cells. In particular, the compounds inhibit tumor growth, inhibit metastasis of tumor cells, and regress tumors.

"Phenotypic expression" is defined herein as the manifestation of an "entire range of physical, biochemical and physiological characteristics of an individual as determined both genetically and environmentally," in contrast to "genotypic expression", which in the art solely refers to the expression of the chromosomal sequence. [See, for example, *Dorland's Illustrated Medical Dictionary*, 26th Edition, 1974, W. B. Saunders, Philadelphia]. Biological activity of the vitaletheine modulators thus includes modulation of the expression of genetic material as influenced by the condition and environment of each cell.

2. Discussion of Related Art

Cancer (neoplasia) is popularly treated with chemotherapeutics, debulking, and/or radiotherapeutics, the efficacy of which is primarily dependent upon differences in growth rates between normal and neoplastic cells. These therapies have proven to be marginally effective. More recent therapies have sought to fortify bodily defenses against developing tumors, for example by enhancing immunological responses of the body postulated to be belligerent to neoplastic cells. Only in part due to the complexity of the immune system, such therapies have not as yet proven their value. There is circumstantial evidence that NK (natural killer) cells may be important effector cells against tumor development in the early stages as described in *Immunobiology of Natural Killer Cells*, volumes I and II, 1986, CRC Press, Inc., Boca Raton, Fla., U.S.A., incorporated herein by reference. There is also evidence that through adoptive immunotherapy (the removal, in vitro activation, and return of immunologically reactive lymphoid cells to the affected animal) the regression of established tumors in the animal can be mediated as described in *Immune Responses to Metastases*, volumes I and II, 1987, Boca Raton, Fla., U.S.A., incorporated herein by reference. It is accordingly desirable to provide a method for normalizing cellular function to interrupt underlying mechanisms of cellular transformation to neoplastic cells, and to identify and enhance, either in vivo or in vitro, those biological responses antagonistic towards neoplastic cells.

SUMMARY OF THE INVENTION

The invention provides a method of treating cancer comprising administering, in vitro or in vivo, a compound or compounds of the group comprising "vitaletheine modulators" which include vitaletheine, a free acid or salt of N-(2-mercaptoethane)-[3-(carboxyamino)-propanamide]; vitalethine, the oxidized (or disulfide) form of this compound; biologically-active or -activatable rearrangement forms of these compounds and biologically-compatible salts, hydrates, and oligomers thereof to a mammal, especially a human, for example to alleviate the pain or distress associated with neoplasia, to inhibit tumor metastasis, to inhibit tumor growth, and to regress tumors. The modulators further include biologically-active or -activatable homologues or analogs of vitaletheine or vitalethine and their corresponding rearrangement forms, including salts, hydrates, and oligomers thereof.

The compounds are useful, inter alia, for promoting phenotypic expression of normal and neoplastic cells, normalizing neoplastic cells, and/or eliminating these cells from the body.

BRIEF DESCRIPTION OF THE DRAWING

In the following Figures, mice are injected three times per week, and error bars illustrate the standard error of the mean.

DETAILED DESCRIPTION OF THE INVENTION

I. The Compounds

Figure 1:
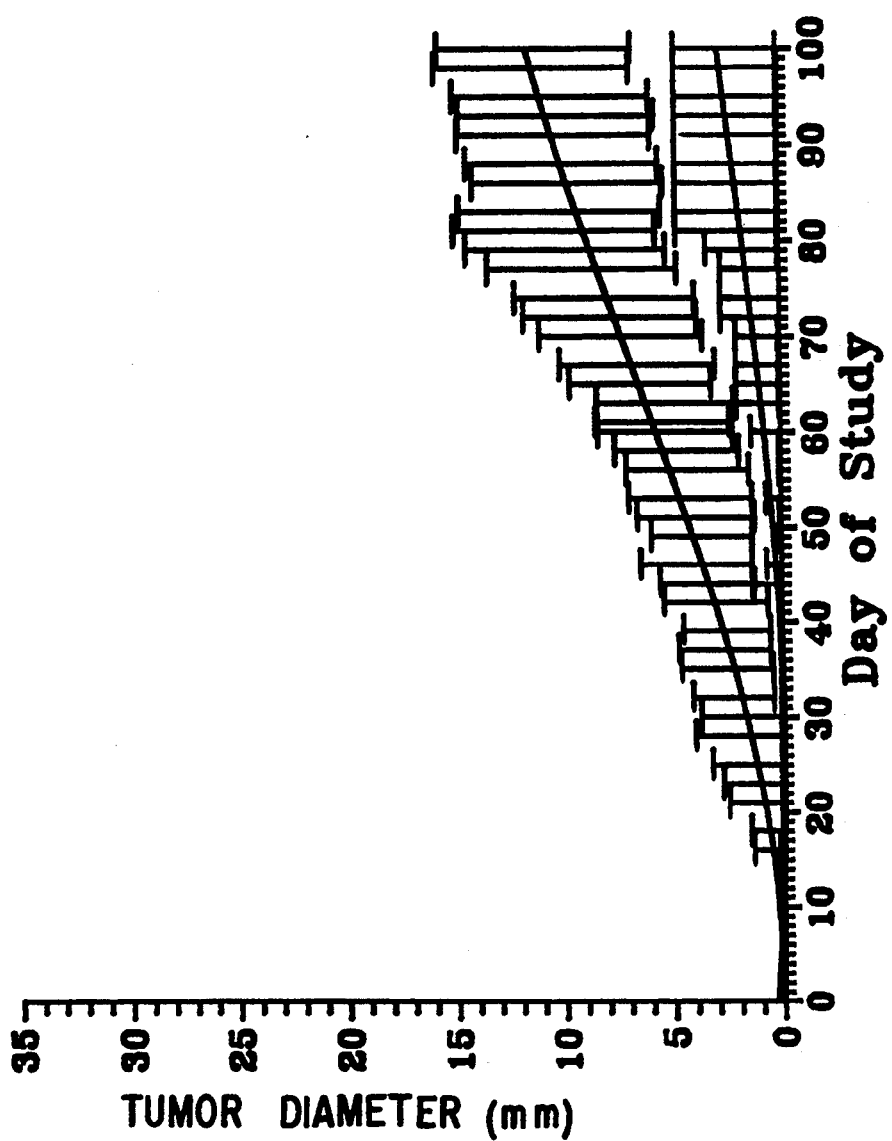
FIG. 1 illustrates average basal development of Cloudman S-91 Melanoma in young (top curve) and old (bottom curve) (Balb c×DBA) mice injected with saline.

The compounds comprise biologically-active or -activatable sulfur-containing hydrocarbon derivatives of a carboxy-amino-amide of the Formula I, hereinafter referred to as "vitaletheine modulators" or "modulators":

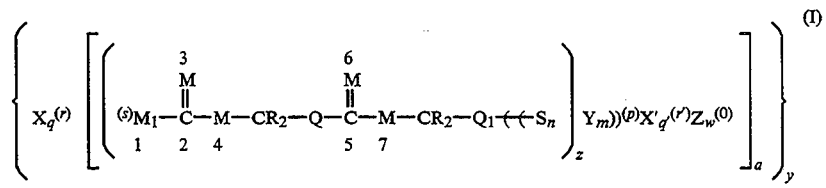

wherein:

the set of double parentheses brackets the portion of the molecule bearing a charge p when z is 1;

the expression M$_1$—(C≡M)—M— (wherein C is the #2C) represents M$_1$—(C≡M)—M—, M$_1$═(C—MA)—M—, or M$_1$—(C—MA)═N—, and —(C≡M)—M— (wherein C is the #5C) represents —(C≡M)—M— or —(C—MA)═N—; wherein A is X, −1 or a direct bond with the proviso that when —(C≡M)—M— is —(C—MA)═N— or the compound is polymeric or internal cyclic or spirocyclic, A is optionally R; and M and M$_1$ are as defined below;

each R is independently H or a hydrocarbon radical as further defined herein;

X is a biologically-compatible cation or cationic complex as further defined herein;

X' is a biologically-compatible ion or ionic complex as further defined herein;

M is S, O, N, or NH;

M$_1$ is S or O with the proviso that M$_1$ is also optionally N or NH when the compound is polymeric, or internal cyclic or spirocyclic;

Q is CR$_2$ or a direct bond;

Q$_1$ is CR$_2$, CR$_2$CR$_2$, or a direct bond;

Y is O, —[C=O]—R, or a direct bond;

$Z^{(0)}$ is a neutral moiety associated with the remainder of the compound of Formula I;

a is the absolute value of $|r/(r'+p+\Sigma s)|$ with the proviso that when $(r'+p+\Sigma s)$ is $\geq 0$, at least one q or q' is zero such that the sum of any charges on the remainder of the complex is balanced by the charges on the ion or ions, X or X', or the ions, X and X';

m is 0 or a whole integer from +1 to +5;

n is 1 or 2 when z is 1, and n is 1 or 1.5 when z is 2;

p is +1, 0, or −1;

q and q' are each independently +1 or zero;

r and r' are each independently a whole integer from +1 to +4, or r' is a whole integer from −1 to −4;

w is 0 or a whole integer from 1 to 5;

s is −1 or 0;

y is 1 to 40;

z is +1 or +2; and the compound of Formula I has a molecular weight of no more than about 10,000 daltons.

Particularly interesting compounds of the Formula I are those wherein y is from 1 to about 20, especially from about 2 to 10; or wherein the average molecular weight of the compound is no more than about 5,000 daltons, or both; and especially wherein the molecular weight of the compound is at least about 130 daltons.

Preferred compounds according to Formula I are compounds of the Formula II, herein referred to as "vitaletheine compounds":

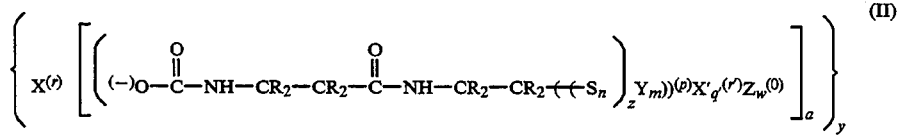

wherein R, X, X', Y, Z, a, m, n, p, q', r, r', w, y, and z are as defined in Formula I.

The vitaletheine compounds include compounds of the Formula II in disulfide forms, comprising homologous or heterologous (mixed) disulfides; trisulfide forms, comprising homologous or heterologous trisulfides; and oxidized forms (m>0) of the homologous or heterologous disulfides or trisulfides, wherein z is 2 and n is 1 or 1.5 according to Formula IIa:

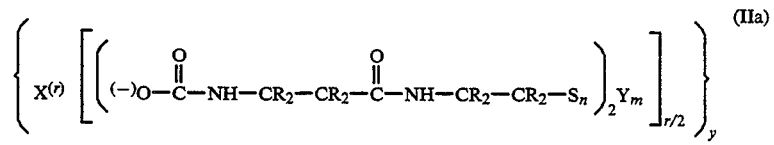

wherein R, X, Y, n, m, r and y are as defined in Formula I.

The vitaletheine compounds further include compounds of the Formula II in reduced and oxidized forms wherein z=1, according to Formula IIb:

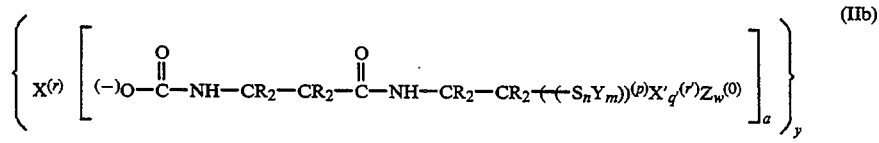

wherein R, X, X', Y, Z, a, n, m, p, q', r, r', w, and y are as defined in Formula II. Particularly contemplated radicals $-((S_n Y_m))^{(p)}$ comprise thioesters and ionized residues of sulfoxy or S-thiosulfoxy acids, especially sulfenic, sulfinic, or sulfonic acids; and when n=2, ionized residues of thiosulfenic, thiosulfoxylic, thiosulfurous, or thiosulfuric acids. Exemplary radicals $-((S_n Y_m))^{(p)}$ include —SOX' (sulfenate), —SX'(thiolate), —SI (sulfenyl iodide), —SI$_3$ (sulfenyl periodide), S$_2$O$_3$X' (thiosulfate); especially SH (thiol or sulfhydryl) and SOH (sulfenic acid). As exemplified above for sulfenyl periodide, a molecule such as I$_2$ or H$_2$O, or other neutral moiety may be associated with $-((S_n Y_m))^{(p)} X'^{(r)}$ or the entire monomer as $Z^{(0)}$.

The modulators include biologically-active or -activatable salts, hydrates, chelates, tautomers, oligomers, and rearrangement forms of the compounds of formulas I, IIa, and IIb, and the corresponding salts, hydrates and chelates of these rearrangement forms. The rearrangement forms of the compounds are primarily internal 5- or 6-membered cyclization products resulting from nucleophilic attack on susceptible atoms including oxidized sulfur and doubly-bonded carbon atoms arising from the tautomerism of the compounds as illustrated in the following Formula IIc:

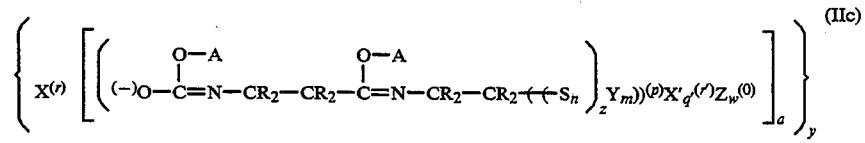

wherein R, X, X', Y, Z, a, n, m, p, q', r, r'w, y, and z are as defined in Formula II; A is R, −1, a direct bond, or X; and either or both of the doubly bonded carbon atoms (2,5) are in the illustrated tautomeric form.

Compounds of formulas I or II, wherein one or more of the atoms O, M, N, or S are rendered nucleophilic, are readily produced in vivo and in vitro where they tend to form internal cyclization products, typically stabilized by hydrogen bonds (including hydrates), ions (salts or chelates), or both. These cyclic compounds include apparently biologically-inactive but -activatable "storage" forms of compounds of the formula I or II, which are easily rearranged to the corresponding active compound. Compounds of the Formulas I and II and subformulas thereof are typically internally cyclized through S or Y, wherein p is zero, or through $M_1$—(C=M)—M— or —(C=M)—M—, as illustrated in the Formulas Ia' and Ib' and following formulas:

an oxidized sulfur atom, thereby forming a spirocyclic urethane by displacing S as illustrated in Formula Ia'; or by displacing S or Y, and X' or Z or both X' and Z as illustrated in Formula Ib'; in all cases z or n or both are 1 after cyclization of the compound. In a similar fashion, the central doubly-bonded carbon (5) can be attacked by one of the nucleophilic atoms S or Y (Formula Ib'), to produce a thiazolidine, or a sulfoxy or thiosulfoxy acid ester, respectively. In this latter case, a spirocyclic urethane is produced when the resulting charge on the central nucleophile (6) attacks the left terminal doubly-bonded carbon atom (2) resulting in the displacement of, for example, $H_2O$, $H_2S$, or $NH_3$ from the structure. Similarly, the charge or developing

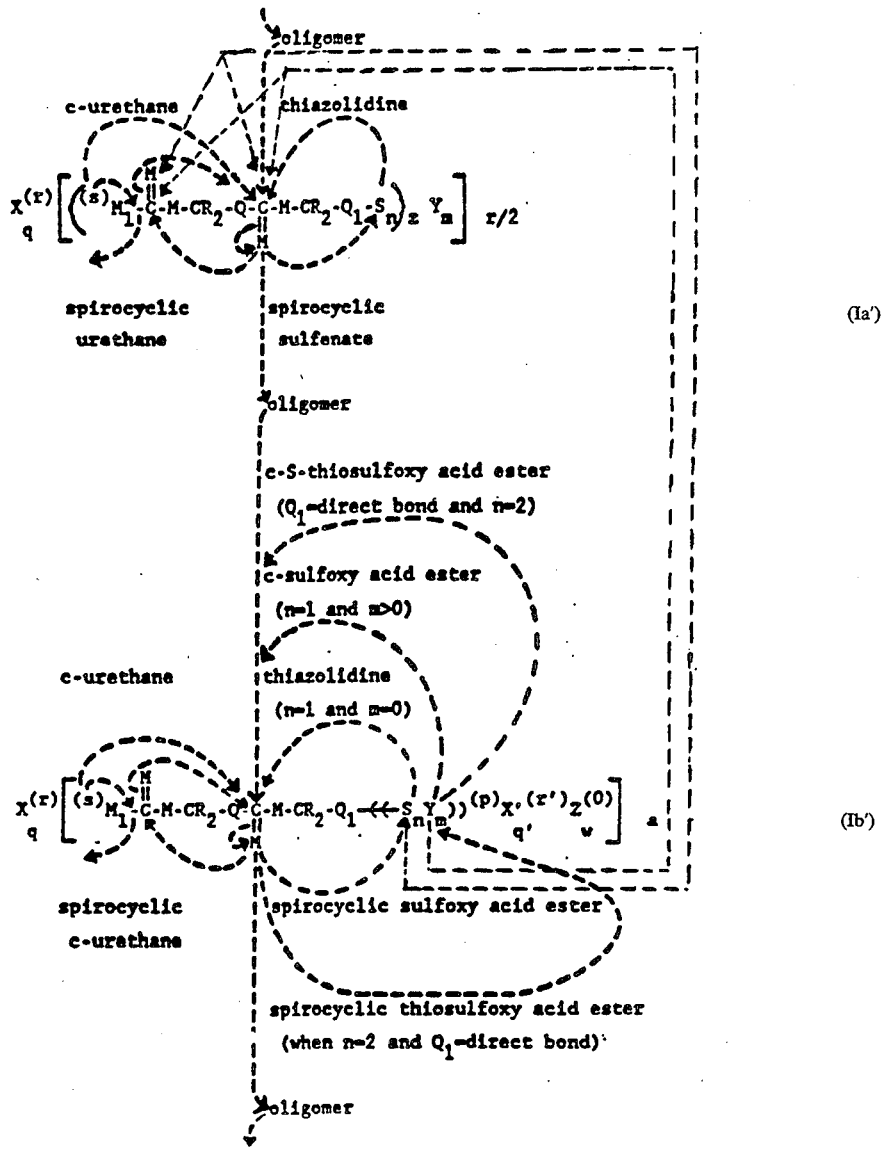

wherein, in the Formulas Ia' and Ib', M, $M_1$, Q, $Q_1$, R, X, X', Y, a, n, m, p, q, q', r, r', s, w, and z are as defined in Formula I; and "c" denotes cyclization.

In general, to form a cyclic urethane of a compound of the Formula I, the charge(s) on the left terminal nucleophile $M_1$ (1) moves to the other nucleophile M (3), either of which may attack the doubly-bonded carbon (5) in the middle of the molecule. The developing charge on the central nucleophile M (6) then picks up an R or X group to form a urethane, or goes on to attack charge on either a central or terminal nucleophile (atoms 3 or 6, respectively) permits attack upon another monomer of the Formula I to form a dimer, which in turn is capable of polymerization to an oligomer, as described below.

Compounds of the Formula II, including the subformulas thereof, are referred to herein as "vitaletheine compounds". The reference compound, herein referred to as "vitaletheine", and its oxidized form, herein referenced to as "vitalethine,", are believed to be the primary biologically-active forms of these compounds. Oligomers of vitaletheine containing from about 2 to about 20 monomers, preferably from about 2 to about 10 monomers, and especially from about 2 to 4 monomers are of particular interest, particularly for their stability. Vitalethine is characterized by the structural Formula IId wherein R is H and y is 1:

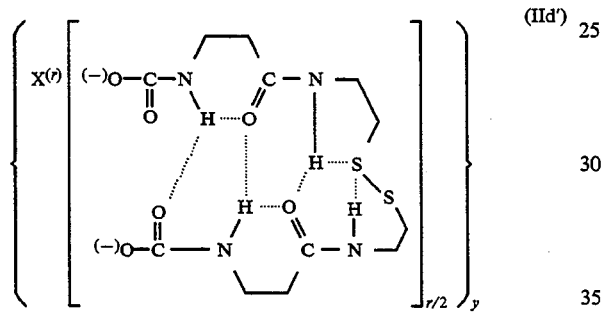

wherein R, X, r and y are as defined in Formula II. Particularly interesting compounds of the Formula IId are those wherein R is H, and X is $Zn^{+2}$, $Ca^{+2}$, $(CaI)^+$, $(CaOH)^+$, or other cationic complex, and wherein y is 1. The cationic groups and the hydrogen bonding illustrated in the following Formula IId' for vitalethine (y=1) appear to add overall structural stability to the otherwise labile carboxy-amino bond:

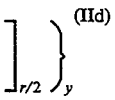

(Dotted lines indicate hydrogen bonding)

Disulfides, sulfenic acids, and sulfenates of Formula I are readily reduced to the corresponding free thiols, particularly in reactions catalyzed by endogenous enzymes, especially reductases and thiol-disulfide isomerases; in particular, vitalethine (Formula IId) is readily reduced to vitaletheine (Formula IIe wherein R is H and y is 1):

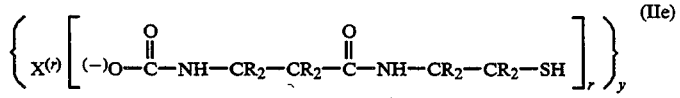

wherein R, X, r and y in Formulas IId, IId', and IIe are as defined in Formula II. Exemplary preferred cations X include $Zn^{+2}$, $Ca^{+2}$, or a cationic complex such as $(CaI)^+$ or $(CaOH)^+$, especially $Zn^{+2}$.

Particularly interesting compounds include oligomers wherein y is from 2 to about 10, especially from 2 to 4, and, more especially, also wherein R is H. Oligomers of the compound of the Formula IIe wherein y is 4 appear to have great biological potency; such oligomers are referred to herein as vitaletheine $V_4$, which refers to compounds of the Formula IIe wherein y 4, and more particularly refers to compounds of the Formula IIe wherein y is 4, R is H, and X is a calcium or zinc cation, or a cationic complex, as discussed in more detail below.

Exemplary biologically-activatable forms of compounds of the Formula II, which may be activatable in vivo or in vitro or converted to vitaletheine of the Formula IId or IIe, include:

1) a disulfide of a cyclic urethane of Formula IIf:

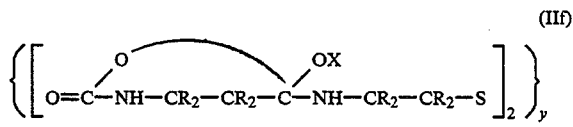

This compound appears to be stabilized as a chelate according to the following model:

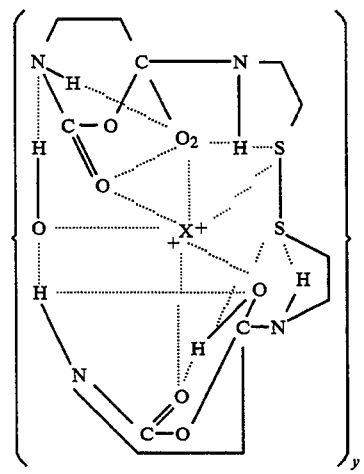

(Dotted lines indicate ionic or hydrogen bonding)

wherein R, X, and y are as defined in Formula II, especially wherein X is $Mg^{+2}$ and wherein the chelate is an $Mg(OH)_2$ chelate;

2) a dehydrate of compound IIf, comprising a cyclic urethane imine of the Formula IIf':

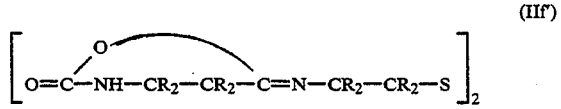

wherein R is as defined in Formula II;

3) a hydroxythiazolidine of the Formula IIg:

wherein X, R, y, and r are as defined in Formula II and A is R, X, a direct bond, or −1 as defined in Formula IIc;

4) a thiazoline of the Formula IIg', in which Formula IIg is dehydrated to the thiazoline in a manner similar to the dehydration of compounds of the Formula IIf to compounds of the Formula IIf';

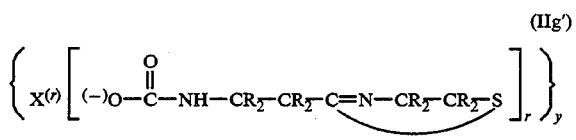

(IIg')

wherein X, R, r, and y are as defined in Formula II;

5) an ionized hydroxythiazolidine of the Formula IIh, as follows:

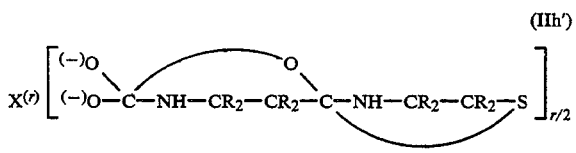

(IIh)

wherein R, X, r, and y are as defined in Formula II; or forms of the thiazolidine of Formula IIh in which the cyclization propagates through the carboxy-amino moiety as in Ia' to form:

a) intermediates of the Formula IIh':

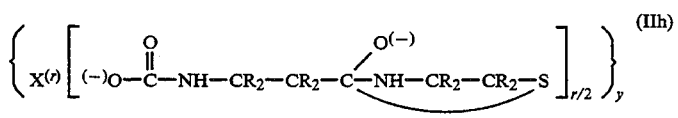

(IIh')

which are dehydratable to:

b) a spirocyclic urethane-thiazolidine of the Formula IIi:

or c) an imidocarbonate tautomer of the Formula IIi':

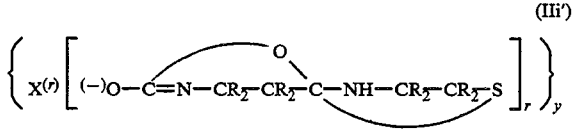

(IIi')

wherein X, R, r, and y in the Formulas IIh', IIi, and IIi' are as defined in Formula II.

Other potentially activatable rearrangement forms of vitaletheine include the following:

6) sulfenates corresponding to the cyclic urethanes of the Formulas IIf and IIf' of the Formulas IIj and IIj':

(IIj)

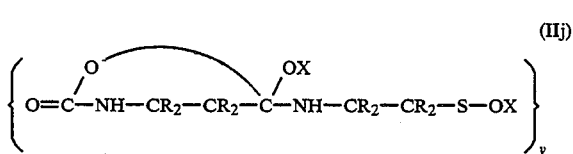

(IIj')

7) cyclic sulfonates corresponding to the thiazolidines of Formulas IIg, IIh, and IIh' of the Formulas IIk, IIm, and IIm':

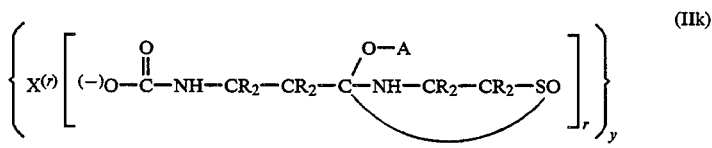

(IIk)

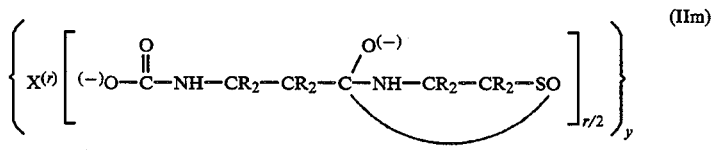

(IIm)

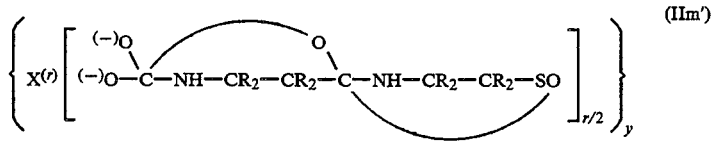

(IIm')

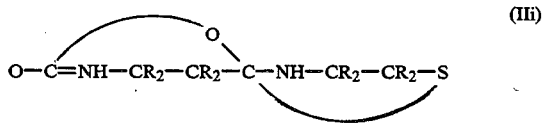

(IIi)

which are dehydratable to:

8) the corresponding dihydro-oxathiazine of Formula IIk':

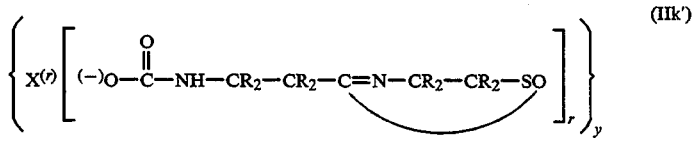
(IIk')

or
9) the corresponding:
   a) spirocyclic urethane-sulfenate of the Formula IIn:

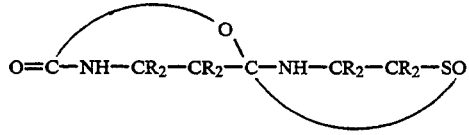
(IIn)

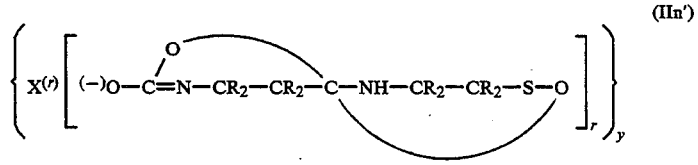

b) or the corresponding imidocarbonate tautomer of Formula IIn':

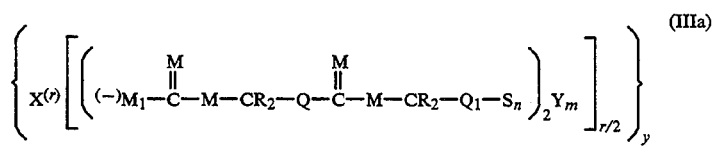
(IIn')

wherein X, R, r, and y in the Formulas IIj through IIn' are as defined in Formula II, and A is as defined in Formula IIc; and the various Formulas II further include rearrangement forms as described herein, particularly as described for Formulas Ia' and Ib'.

The modulators further comprise biologically-active and -activatable derivatives of the vitaletheine modulators of the Formula I, characterized by the following Formula III, herein referred to as "vitaletheine derivatives":

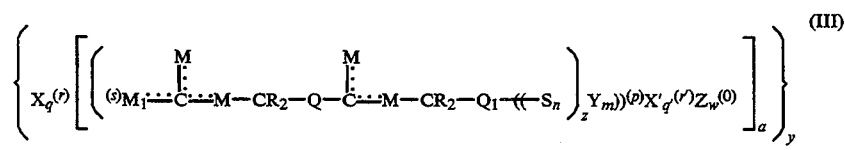
(III)

wherein $M_1$ is S or O; M is S, O, N, or NH; at least one $M_1$ or M is other than O; and R, Q, $Q_1$, X, X', Y, Z, a, n, m, p, q, q', r, r', s, w, y, and z, are as defined in Formula I; wherein the dotted lines are bond resonances or tautomerisms; and wherein in compounds of the Formula III which are internal cyclic and spirocyclic compounds, $M_1$ is additionally optionally M as depicted in Formulas IV through VIe'.

Particular derivatives within the scope of Formula III include homologous or mixed sulfides, homologous or mixed trisulfides, and oxidized forms (m>0) of the homologous or mixed disulfides or trisulfides, wherein z=2 and n is 1 or 1.5 according to Formula IIIa:

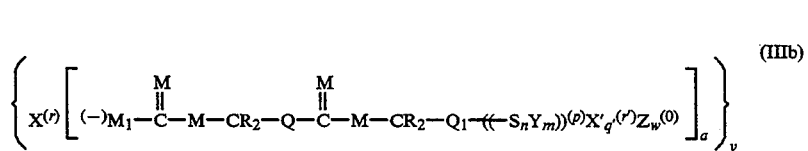
(IIIa)

wherein M, $M_1$, Q, $Q_1$, R, X, Y, m, n, r, and y are as defined in Formula III; and X is especially $H^+$, $Zn^{+2}$, calcium cation, or a calcium cationic complex.

Further derivatives within the scope of Formula III include the reduced and oxidized forms of compounds of Formula III wherein z=1, according to the Formula IIIb:

$$\left\{ X^{(r)} \left[ (-)M_1 - \overset{M}{\underset{\|}{C}} - M - CR_2 - Q - \overset{M}{\underset{\|}{C}} - M - CR_2 - Q_1 -\!\!(\!\!-S_nY_m))^{(p)}X'_{q'}{}^{(r')}Z_w^{(0)} \right]_a \right\}_y$$ (IIIb)

wherein M, $M_1$, Q, $Q_1$, R, X, X', Y, Z, a, m, n, p, q', r, r', w, and y are as defined in Formula III, and X is especially $H^+$, $Zn^{+2}$, calcium cation, or a calcium cationic complex.

The compounds of the Formula III also include these compounds in the form of their biologically-active or -activatable tautomers, chelates, hydrates, and biologically-compatible salts as described for Formulas I and II, and rearrangement products thereof, including compounds based on nucleophilic cyclization according to Formulas Ia' and Ib'; and further include tautomeric derivatives of compounds of the Formula III as described for Formula IIc, as summarized in Formula IIIc:

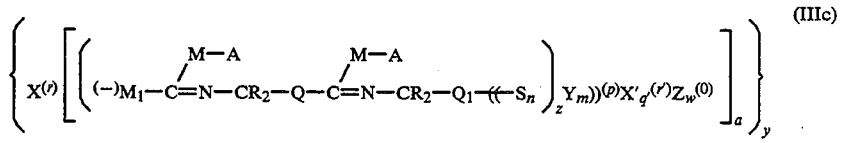
(IIIc)

wherein M, M₁, Q, Q₁, R, X, X', Y, Z, a, m, n, p, q', r, r', w, y, and z are as defined in Formula III, A is as defined in Formula IIc, and either or both doubly bonded carbon atoms (2,5) are in the illustrated tautomeric form.

Additional compounds include modulators of the Formulas IV–VI, and the subformulas thereof, wherein M₁ in the compounds of the Formula I is M:

(IV)

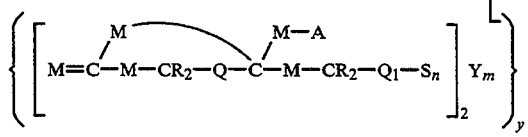

wherein M, Q, Q₁, R, Y, m, n, and y are as defined in Formula I and A is as defined in Formula IIc.

Further compounds comprise biologically-active and activatable compounds of the Formula V:

(V)

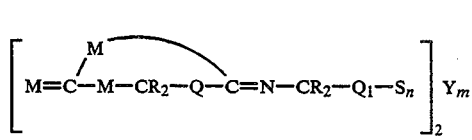

wherein M, Q, Q₁, R, Y, m and n are as defined in Formula I.

The compounds further include biologically-active and -activatable forms of compounds of the Formulas VI and the following thereof in reduced and oxidized forms, which comprise:

1) cyclic urethanes of the Formula VI:

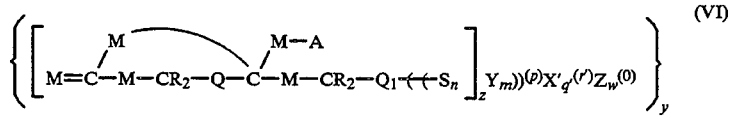
(VI)

wherein the urethanes are substituted as defined in Formulas IIf, IIg, and IIh; M, Q, Q₁, R, X, X', Y, Z, m, n, p, q', r', w, y, and z are as defined in Formula I, and A is as defined in Formula IV;

2) cyclic imines of the Formula VIa comprising urethanes dehydrated as analogously illustrated in Formulas IIf and IIf':

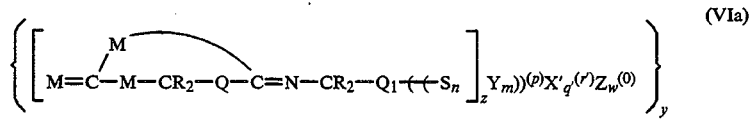
(VIa)

wherein M, Q, Q₁, R, X', Y, Z, n, m, p, q', r', w, y, and z are as defined in Formula I;

3) spirocyclic compounds of the Formulas VIb and VIc analogous to precursors of the spirocyclic urethanes of the Formulas IIh' and IIn:

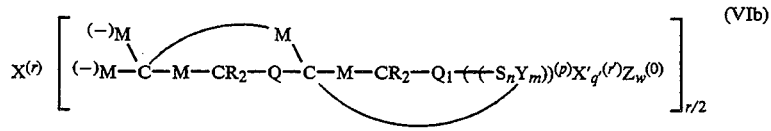
(VIb)

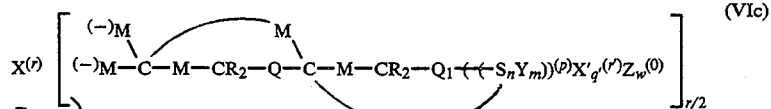
(VIc)

wherein M, Q, Q₁, R, X, X', Y, Z, n, m, p, q', r, r', w, and z are as defined in Formula I;

4) corresponding spirocyclic urethane-sulfoxy (n=1) or urethane-thiosulfoxy (n=2) acid esters (Formula VId), or urethane-sulfides (Formula VIe), respectively, formed by elimination of sulfide, nitride, or oxide from the compounds of the Formulas VIb and VIc as H₂S, H₃N, or H₂O:

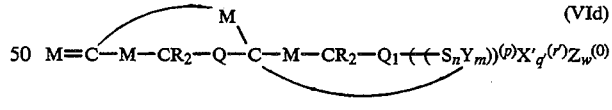
(VId)

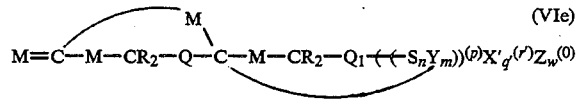
(VIe)

wherein M, Q, Q₁, R, X', Y, Z, m, n, p, q', r', and w are defined as in Formula I; or 5) imidocarbonate tautomers of compounds of the Formulas VId or VIe, as described for Formula IIi':

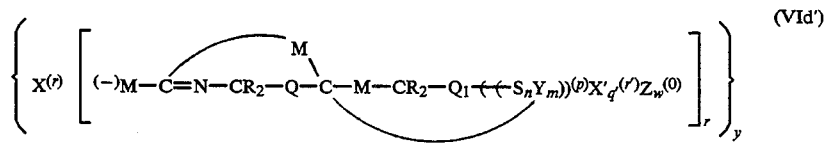

(VId')

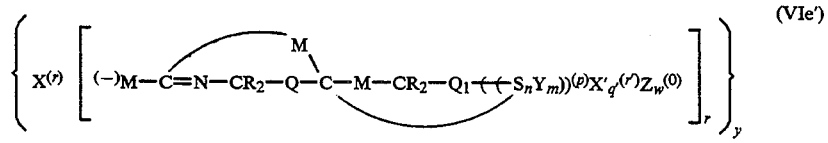

(VIe')

wherein M, Q, $Q_1$, R, X, X', Y, Z, m, m, p, q', r', w, y, and z are as defined in Formula I.

The modulators especially include biologically-active or -activatable salts, hydrates, chelates, tautomers, and rearrangement forms of oligomers of monomers of the Formula I, particularly oligomers of monomers of the Formula IId, herein referred to as "vitaletheine oligomers", comprising polymerization products of monomers of the Formula I and subformulas thereof, including cyclizations according to Formulas Ia' and Ib', and the corresponding salts, hydrates, tautomers, and chelates of these forms. Oligomers produced by the polymerization exemplified in Formulas Ia' and Ib' appear to be resistant to rearrangement and provide storage forms of compounds, which, however, may still be labile to certain organic solvents such as ethers and alcohols. Preferred oligomers of monomers of the Formula I and subformulas thereof are those wherein y is from about 2 to 10. Particularly useful preparations of vitaletheine, include those prepared, for example, according to Example III, especially those comprising a vitaletheine oligomers of 4 monomers (y=4 in Formula IIe and Formula IX following), and particularly optionally including minor proportions of at least one other oligomer or compound described herein. This tetramer and vitalethine appear to be particularly active. Formation of this oligomer (herein referred to as "V4") appears to occur through an initial nucleophilic attack of a first monomer on one of the doubly-bonded carbons (2,5) of a second monomer to generate a nucleophilic oxygen from the carbonyl oxygen (6) of the second monomer. Polymerization of the monomers of Formula I and the subformulas thereof, for example oligomers wherein y is about 20 or less, appears to be propagated through this initial alkoxide ion (the nucleophilic oxygen 6 resulting from the initial dimerization) until the polymer folds back on itself and the last alkoxide ion present (the fourth in the case of $V_4$) reacts with the first (initiating) monomer. An intermediate dimer, exemplified in Formula VII, is comparable to a benzyl derivative of Formula VIII, obtained as a by-product under certain conditions (see, e.g., Examples IIA, and IX) in the synthesis of vitaletheine $V_4$:

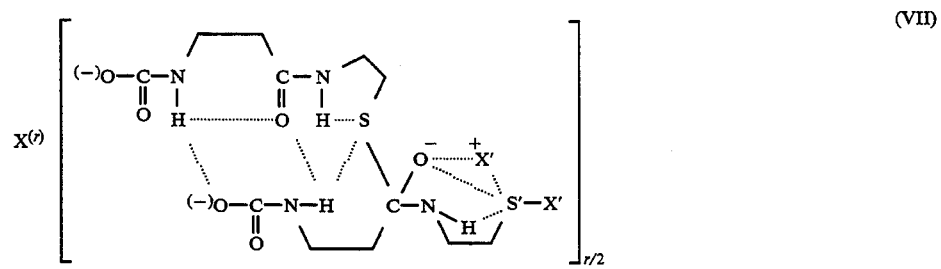

(VII)

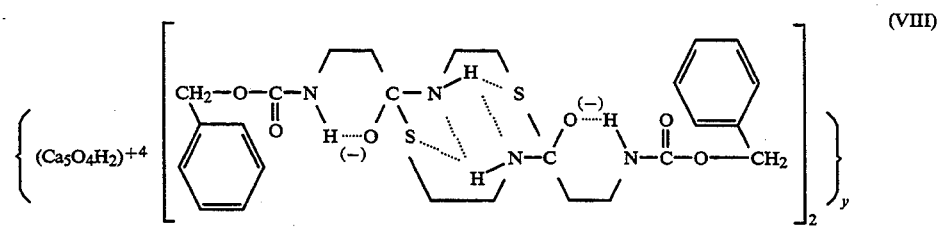

(VIII)

The monomers alternately are linked by Y when Y is the initial attacking nucleophile, according to Formulas Ia', Ib' and X.

The reaction terminating the polymerization is apparently a nucleophilic substitution of the original nucleophile involved in the formation of the first alkoxide ion by the last alkoxide ion, resulting in a cyclic polymer of monomer subunits, which are nearly identical in spectroscopic analyses. Once formed, the polymer appears to stabilize the carboxy-amino moieties through salt brides within the oligomer, and sterically prevents rearrangement to other active or activatable forms. Vitaletheine V4 (the tetramer of vitaletheine, Formula IIe) is illustrated in the following Formula IX:

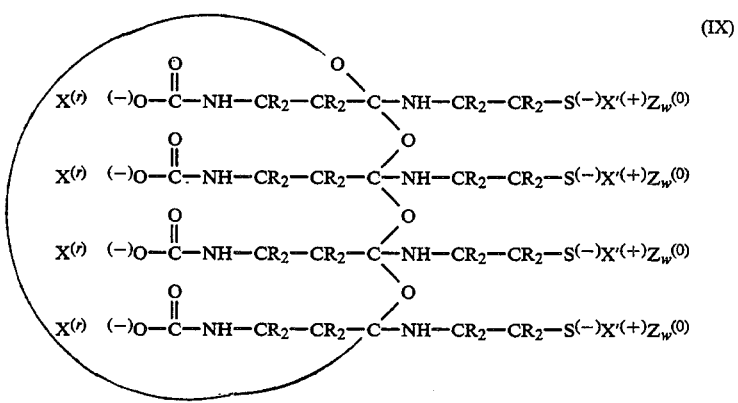

(IX)

wherein R, X, X'$ Z, r, and w are as previously defined in Formula I; preferably X or X' is a portion of the cation $Zn^{+2}$ having a charge of $+1$ and X' or X, respectively; is $H^+$; and especially when X' is a portion of $Zn^{+2}$, X is $H^+$, r is $+1$, Z is H2O, and w is 2. In the preparation of vitaletheine $V_4$ as described in Example III, 4 $H^+$ and 2 $Zn^{+2}$ neutralize the amino-carboxylate and thiolate charges, and the entire complex contains 8 moles of hydration per mole of complex.

Decomposition or rearrangement of vitaletheine $V_4$ is induced by some organic solvents such as ether, and by heating, which apparent results in decarboxylation of the polymer. Accordingly, caution should be exercise during purification procedures to obviate loss of product.

The modulators further include biologically-active and -activatable derivatives of the vitaletheine oligomers of the following Formula X, wherein a compound of Formula III is polymerized as a monomer via nucleophilic attack on one of the doubly-bonded carbons (2,5):

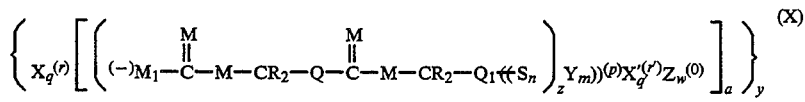

(X)

wherein the attacking nucleophile(s) comprise(s) $M_1$ (1), M (3,6), S, or Y as described for Formulas Ia', Ib', VII, VIII, and IX, and arise through the tautomerizations described herein, particularly as described for Formula IIIc; and wherein M, $M_1$, Q, $Q_1$, R, Y, X, X', Y, Z, r, n, z, m, p, q, q'$ r', a, w, and y are as defined in Formula I.

In compounds of the Formulas I through X, and the various subformulas thereof, the hydrocarbon radical R is substituted or unsubstituted, saturated or unsaturated, with the provisos that the compounds have a molecular weight of no more than about 10,000 daltons and contain less than about 40 monomers (y<40); preferably, the compounds have a molecular weight of no more than about 5,000 daltons and contain less than about 20 monomers (y<20); most preferably, the compounds have a molecular weight of at least about 130 daltons; compounds containing from about 2 to 10 monomers are especially interesting. Further, any hydrocarbon substituents R present must not substantially adversely affect the biofunction of the molecule, either chemically or stereochemically.

Preferably, hydrocarbon substituents R comprise suitable lipophilic moieties which counterbalance the hydrophilic portions of molecule to promote the transfer of the modulator across the cell membrane to maximize the intracellular reactions as understood by those skilled in the art. Further, R is most preferably selected to avoid stereochemical obstruction or biochemical inactivation of the active functional groups of the molecule, particularly the carboxyl-terminus and sulfur-terminus moieties which are apparently critical to the biological function of the molecule, both in their chemical constituents and their physical presentation to the cell. The substituents R are thus not critical, as long as these groups minimally function as described, do not substantially interfere with the biological activity of the molecule, do not substantially promote decomposition or unwanted side reactions of the molecule, either intracellularly or extracellularly, and do not substantially render the molecule toxic to the cell; such hydrocarbon radicals R are referred to herein as "physiologically-acceptable hydrocarbon radicals R".

Exemplary hydrocarbon substituents R are $C_1$-$C_{20}$-hydrocarbons, especially $C_1$-$C_{18}$-aliphatic or -cycloaliphatic radicals, which are branched or unbranched, substituted or unsubstituted, saturated or unsaturated, particularly $C_1$-$C_{18}$-alkyl or -alkenyl; or substituted or unsubstituted mononuclear or polynuclear aryl, especially phenyl. An exhaustive list of potentially suitable hydrocarbon radicals R is set forth in U.S. Pat. No. 4,216,160 to Doru, et al., incorporated herein by reference, especially the hydrocarbon radicals $R_1$ and $R_2$ described therein. A particularly suitable substituent R is H.

In the compounds of the Formulas I through X, X or X' is $H^+$, hydronium or a cation or an organic or inorganic cationic complex; or X' is additionally an anion or an organic or inorganic anionic complex; and each X or X' is selected for biological compatibility. The cation or cationic complex X is monovalent, divalent, or polyvalent, especially monovalent, divalent, or trivalent wherein r is $+1$, $+2$, or $+3$; the ion or ionic complex X' is monovalent, divalent or polyvalent, especially monovalent, divalent, or trivalent wherein r' is $-3$ to $-1$ or $+1$ to $+3$. X or X' each comprises an ion or ionic complex which does not substantially irreversibly inactive the active portion of the molecule and which does not substantially interfere with the biofunction of the active remainder of the molecule, either chemically or stereochemically; such ions or ionic complexes X or X' are referred to herein as "biologically-compatible ions". Some ions may inactive the molecule while they are present, but the inactivation is readily reversed, for example spontaneously, enzymatially, or chemically; such ions or ionic complexes are contemplated to be useful, as it may be convenient to prepare an inactive molecule and subsequently active it for use, especially in the preparing of molecules targeted for activation and use in specific cells or tissues. Modulators in solution are highly sensitive to electrolyte concentrations, and are easily irreversibly inactivated by excess amounts of compounds or many electrolytes, particularly magnesium ions. Further, the ions X and X' may shift an existing equilibrium between a biologically-active form of the modulator and a corresponding storage form of the modulator in favor of the storage form, or vice versa. Exemplary cations X which appear to stabilize the molecule in either active or activatable form include $Ca^{+2}$, $(CaI)^+$, and especially $Zn^{+2}$, which favor the active form, and $Mg^{+2}$, which may favor an activatable or storage form. Exemplary ions X' include $H^+$, $I^-$, periodide ($I_3^-$), $Zn^{+2}$, or $Ca^{+2}$. As described herein, a charge $> +1$ on the ion X or X' may be apportioned between two or more negative charges s or p on the remainder of the molecule to form one or more salts bridges within the molecule or between molecules; the "ion X'" in this instance accordingly comprises a portion of the ion X, or vice versa. A positive ion X or X' having a charge greater than $+1$ may form a bridge between a group beawring a charge of s wherein s is $-1$ and a group bearing a charge p wherein p is $-1$ in a given molecule, or between two groups bearing the charge s wherein s is $-1$, including molecules wherein $y=1$; or in molecules wherein $y>1$, they may form a bridge between two groups bearing a negative charge s, or two groups bearing a negative charge p, or between two groups one bearing a negative charge s and the other bearing a negative charge p. When p is $+1$, an ion X' having a charge less than $-1$ may also form a bridge between two groups bearing a positive charge in the same molecule. Additionally, an ion X or X' may chelate two identical or different monomers or oligomers of the Formula I. Generally, the total charges on the ions X and X' present will balance the total charges s and p on the molecule; however, in some instances, a portion of the total charge on the molecule may be balanced by one or more ions extraneous to the molecule.

In compounds of the Formulas I through IX, the neutral moiety $Z_w^{(0)}$ is a neutral molecule or another neutral moiety which is associable with the compound of the Formula I and subformulas thereof as indicated. Exemplary neutral moieties $Z_w^{(0)}$ include for example, iodine, $H_2O$, polyethylene glycols, and polyoxyethylene ether detergents.

Several inactive but activatable forms of the modulators within the scope of Formula I have been identified, including those described above, which appear in some instances to be inactive "storage" forms of the modulators, capable of in vivo or in vitro rearrangement to one or more active forms. In vivo rearrangement or in vitro rearrangement in the presence of living cells appears to be a result of the action of endogenous enzymes as mentioned above, which, depending upon the type of cell or cells and culture conditions, may convert inactive forms of the compounds to the corresponding active form, especially in the case of the vitalethine or vitaletheine compounds. Proteins and hydrophobic environments such as cell membranes may associate with and stabilize the active form of the product. Rearrangement of inactive but activatable forms may also be induced by other means as described below.

Within the present context, "biologically-active or -activatable" refers to compounds within the scope of Formulas I through X and the subformulas thereof which are biologically active, or which are activatable to biologically active compounds on exposure to activators such as the following: chemicals including biochemicals such as enzymes and selected organic solvents, acids, and bases; radiating including electromagnetic, actinic, or radioactive energy; or heat energy. Inactive compounds which respond to such treatment to become bioactive are referred to herein as "activatable" and are included within the scope of Formulas I through X.

Certain compounds, and other substances which are postulated to inhibit the degradation or metabolism of the modulators, are useful in combination with the modulators of Formulas I through X. At low concentrations especially, degradation catalyzed by endogenous enzymes represents a mechanism for significant losses of added modulator. Compounds which inhibit these enzymes, without themselves interfering with the action of the modulators, potentiate the action of the modulator by making sustained, low, effective concentrations possible.

II. Preparation of the Compounds

The compounds, particularly those of the Formula IIe wherein R is H, are postulated as endogenous to a substantially complete spectrum of plants, animals, and microorganisms, and, accordingly, it is contemplated that the compounds are recoverable from a variety of organisms and isolatable for use according to methods well-understood in the art. It is further contemplated that the recited bioapplicability of the compounds to the function of the broad spectrum of cells recited below is attributable to the ubiquitous, or near-ubiquitous presence of these compounds in virtually every living cell and the essential presence of these compounds for the autoregulation of cellular life. However, since the endogenous compounds are though to be present, in vivo, in extremely small amounts, and are known to be easily converted into inactivatable forms, for example by customary purification methods, it is recommended that the compounds be synthesized for use, especially to avoid contamination of the product with mitogens, saponins, pathogens, antigens or other potentially reactive compounds present in biological materials, and to prevent the undesirable rearrangements described above.

At present, the most potent of these compounds appear to be those within the scope of Formula IId, viz., those based on the bis anionic vitalethine [N,N'-(dithiodi-2,1-ethanediyl)-bis-(3-carboxyamino-propanamide)] also designated as 3,3'-[dithiodi[(2,1-ethanediyl)amino]]-bis-[N-(3-oxo-3,1-propanediyl-carbamic acid], and polymers of vitaletheine. Analysis of the polymers by filtration through a P-2 gel column indicates that the monomer of vitaletheine (Formula IIe) tends to spontaneously polymerize during purification to form multimers, especially oligomers wherein y is from 2 to 4; the preparations of the $V_4$ oligomer and vitalethine, especially, have extremely high biological activities.

The [13C]-NMR of vitaletheine $V_4$ (Formula IIe or IX, wherein y is 4 and R is H) indicates nearly homologous subunits; the tetramer ($y=4$) is an extremely rigid structure similar to those reported for certain ortho-ester-like compounds in Tetrahedron Letters 22:4365–4368 [1981] (incorporated herein by reference). Based on [13C]-NMR analysis, the multimeric vitaletheine structures are postulated to be polymers which are formed by the attack of nucleophilic oxygen (6) derived from the central amide on the carbonyl carbon (5) of another monomer, probably through initial attack on the carbonyl carbon (5) of the amide of the initiating monomer to generate a nucleophilic oxygen (alkoxide ion) from the carbonyl oxygen (6). Polymerization may be propagated through alkoxide ions (in a manner which resembles ortho-ester formation), until the polymer folds back on itself and a terminal alkoxide ion reacts with the original monomer. The polymerization is then terminated by nucleophilic substitution of sulfur or atom Y according to Formula X which initiated the polymerization with a terminal alkoxide ion, resulting a cyclic polymer which typically contains homologous monomer subunits. Slight puckering of the polymerized (—C—O—)$_n$ ring (n is from about 3 to about 24, usually 3 or 4, especially 4) split observed resonances in the above-described NMR analysis of $V_4$ into four minor peaks in the range calculated for a highly constrained quaternary carbon atoms. Polymerization of the monomer does not appear to result from manipulation of the monomer by the applied analytical procedures, since this NMR evidence indicating a tetramer was obtained prior to determination of the molecular weight of the polymer by gel filtration.

BEST MODES FOR PREPARING THE COMPOUNDS

Although vitalethine is also prepared by the above procedure (Examples IIa and IIIa), carboxylation of β-alethine by reacting the disulfide with phosgene in the appropriate chemical milieu is the preferred method of synthesis. Packing of the reaction vessel in dry ice controls the exothermic reaction and improves yields of large-scale preparations. Similarities in the physical properties of these two potent biomodulators, i.e. thermal lability and infrared spectra, are described in Examples III, IV, and V.

The compounds were conveniently prepared employing β-alethine blocked with a protective group such as N,N'-bis-carbobenzoxy-(CBZ—) as starting material. The blocked β-alethine was then selectively deblocked by the process Example IV to remove benzyl groups and yield the desired compounds or precursors. Techniques for the synthesis of the blocked β-alethine starting material are present in the literature; however, the known techniques generally provided a product of low yield or purity, or both. Many of the impurities obtained in known procedures result from the combined poor solubility of the product compound and the dicyclohexylurea by-product produced in coupling reactions which utilize dicyclohexylcarbodiimide.

Product purity and yield are improved by first coupling CBZ— or similarly-blocked β-alanine to N-hydroxysuccinimide (commercially available from Aldrich Chemicals, Milwaukee, Wis., U.S.A.) to produce the corresponding N-hydroxysuccinimide active ester using dicyclohexylcarbodiimide (commercially available from Schwarz/Mann, Orangeburg, N.Y., U.S.A.) following the procedure described in [J. Am. Chem. Soc. 86: 1839–1842 (1962), incorporated herein by reference. Commercially available starting materials, such as N-CBZ-β-alanine (Sigma Chemical, St. Louis, Mo., U.S.A.), are first coupled to N-hydroxysuccinimide (Aldrich Chemicals), with precipitation or the dicyclohexylurea by-product. The soluble active ester product is recrystallized and coupled to the free amino groups of cystamine, readily obtained from cysteamine (available from Aldrich Chemicals) by oxidation with peroxide, for example, by titration in acetonitrile with peroxide until no reducing equivalents are evident. This is conveniently monitored using strips of paper soaked in a solution of 0.1M potassium phosphate buffer and 10 mM, 5,5'-dithiobis-2-nitrobenzoic acid (Sigma Chemical) and dried; residual thiol in the peroxide/cysteamine mixture produces an intense yellow spot on the paper. Water added with the peroxide and produced as a by-product of cysteamine oxidation is readily removed by repeated evaporation of the acetonitrile azeotrope prior to coupling with the soluble N-hydroxysuccinimide active ester obtained by dicyclohexyl-carbodiimide coupling (supra). Using this form of cystamine instead of a hydrochloride or similar salt ensures more complete reaction of the active ester with the cystamine, since this reaction is dependent upon a nucleophilic attack of the free amines of cystamine on the carbonyl carbon of the active ester. N-hydroxysuccinimide is regenerated as a by-product of this reaction as the blocked β-alethine precipitates. The benzyl groups are then removed from the blocked β-alethine as described, for example, in Examples III, IV, and IX, and the product compounds recovered.

III. Utility of the Compounds

The compounds are useful, inter alia, for promoting phenotypic expression of normal and neoplastic cells, normalizing neoplastic cells, and/or eliminating these cells from the body, including, for example, reestablishing normal growth cycles, lifespans, and functions of tumor cells and immune cells in particular, and especially of NK (natural killer) cells.

Specifically contemplated utility categories include a) enhancing the capacity of NK cells to destroy tumor cells, b) rendering tumor cells vulnerable to cells of the immune system, c) prolonging the lifespan of immunocytes belligerent to neoplastic cells, in vivo, and d) interrupting the underlying mechanisms of cell transformation from neoplastic to malignant cells.

Modulator or modulators useful for treating neoplasia according to the method of the invention comprise active- or activatable compounds of the Formulas I through X. As used herein, "active vitaletheine modulators" comprise compounds of the Formulas I through X which per se are effective in vivo or in vitro for the treatment of neoplasia. The term "activatable vitaletheine modulators" as used herein refers to compounds of the Formulas I through X which are not in their initial form active, but are activatable by biological or other means to compounds which similarly are effective for the treatment of neoplasia in vitro in vivo, primarily by rearrangement including reversible cyclization and tautomerization, dehydration, hydration, salt exchange, oxidation, and/or reduction of the compounds as described herein, before the modulators are incorporated in the culture medium, before the compound is administered in vivo, or by appropriate adjustment of the in vitro or in vivo conditions, for example with regard to pH, salt, partial pressure of $O_2$ or $CO_2$, enzyme content, exposure to UV or other radiation, and temperature. The characterization of a given modulator as either "active" or "activatable" for a particular application is dependent on a variety of factors, including environment of the cell and cell type, and selection of modulators for optimum results is made accordingly.

In practice, it is generally preferred to employ naturally-occurring vitaletheine modulators of the Formula II and subformulas thereof, as the derivatives thereof of the Formula III et. seq. are not believed to be endogenous compounds and their metabolic pathways are at present unknown. The naturally-occurring modulators of the Formula II are postulated to be endogenous to a broad spectrum of cells, including animal, plant, insect, arachnid, and microorganisms cells, and accordingly, most, if not all, cells derived from these organisms are expected to have well-established mechanisms for the enzymatic activation, utilization, and metabolism of these compounds. Thus, to maximize efficacy and minimize potentially toxic, undesirable, or even hazardous side reactions, the use of either naturally-occurring modulators of the Formula I or vitaletheine modulators activatable to the naturally-occurring modulators in the practice of the invention is recommended, especially vitalethine, vitaletheine, or vitaletheine $V_4$ of the Formulas IId, IIe, and IX.

The use of modulators in vivo or in vitro according to the present invention in treating neoplasia is contemplated to be applicable to a broad range of cells, owing to the postulated near-universality of precursors to the compounds of the Formula II in the metabolic pathways of at least eukaryotic organisms, especially humans, and the biochemical equivalence of the non-naturally occurring homologs and analogs of Formulas III through VIII.

The effectiveness of the modulators on neoplasia is typically concentration-dependent. Optimization of efficacy may occur within a relatively narrow effective concentration range of modulator; outside this range, neoplasia may be unaffected or exacerbated. Also, the process of the invention may be, at least in some instances, reversible; that is, neoplasia may return to untreated growth after treatment is discontinued.

The amount of modulator eliciting the desired biological response according to the present invention is herein referred to as an "effective amount" of modulator. Optimum amounts of modulator for the treatment of neoplasia are readily determined by introducing varying amounts of modulator into test cultures or, in vivo, and selecting the concentration at which tumors are inhibited.

The modulators may be administered directly to the organism, for example, the mammal, according to the process of the invention, in amounts sufficient to promote the desired biological response by conventional routes, such as parenterally, in any location which does not result in the irreversible inactivation or maladsorption of the modulator$ including i.v., i.p., s.c., and i.d. Likewise, the modulators may be administered in any other fashion which does not result in the irreversible inactivation or maladsorption, such as orally with the appropriate additionally optional entero-coating, rectally, nasally including sprays, and dermally including patches. Standard carriers not affecting compound integrity are useful for administration of vitaletheine modulators, such as physiological saline.

The modulator is administered indirectly according to the process of the invention by removing immunocytes from the afflicted body, treating them in culture as described herein, and reinjecting them according to standard procedures as described in, for example, Immune Responses to Metastases, volume II, chapter 11, 1987, CRC Press, Inc., Boca Raton, Fla., U.S.A., incorporated herein by reference. Preferably the cytotoxicity of the immunocytes towards tumor cells is further enhanced by additional in vitro exposure of the cells either to the tumor cells, especially those derived from the afflicted mammal, or to inhibitors of the metabolism of the modulator or modulators, or to a combination thereof, prior to reinjection. Enhancement of cytotoxicity of immunocytes towards tumor cells is described for example, supra.

According to the method of the invention, cells may be exposed to the modulator or modulators, in vitro, in any convenient fashion. The modulators may, for example, be incorporated into the nutrient medium, or into cell support elements. The cells may also be pre-exposed to modulator. In a particular embodiment of the invention, the modulators are incorporated into a support material by combining the modulators with starting materials employed to prepare the supports. Introduction of modulators into synthetic prepolymers for the production of natural or synthetic supports such as hollow fiber membranes, or pregels for the production of gel supports, or liquefied cellulose for the production of cellulose supports, are exemplary.

Culture media in which vitaletheine modulators are to be incorporated for modulation of cell activity of cells cultured therein do not form a part of the invention. Exemplary useful media include all known culture media and media hereinafter developed which support maintenance and/or growth of the cells therein cultured. Such media typically comprise at least nutrients suitable for the growth of the specific cells to be cultured, a physiological balance of electrolytes, a physiological pH, and water, as necessary to support cell growth, as well as physical culture aids such as cell supports. A variety of other known auxiliaries such as antibiotics, sera, or cell growth regulators may also be included in the basal culture media into which the modulators are to be incorporated, especially those known for enhancing cell propagation, or for augmenting cell growth and/or longevity, including cell growth factors such as peptidyl hormones specific for the cells being cultured, of the type well-known in the art. These and other auxiliaries which affect cell longevity and function in some respects are optically included in the basal culture medium providing that they do not completely obviate the activity of the vitaletheine modulators; in fact, selective proliferation with one or more of these factors, such as, for example, specific peptidyl hormones, in the presence of a vitaletheine modulator to stabilize the cells being generated comprises a useful technique for selectively enriching the cells of interest in a gross cellular extract, for example, organ extracts. Compounds which inhibit metabolism of the modulators may also be included.

Conventional media into which the modulators are incorporated for the practice of the invention are herein referred to as "basal culture media". Basal culture media into which the modulators are incorporated may be employed in conjunction with any suitable culture techniques known or hereinafter to be developed, including batch or continuous culture, perfusion culture, or other techniques, particularly those adapted to maximize cell culture, as by the continuous replenishment of nutrients or other media components and continuous removal of cell waste materials.

Broadly, the modulators are suitable for modulating the activity of cells in any culture medium which supports the growth of these cells and which does not significantly inactivate or otherwise adversely affect the function of the modulators. Culture media employable with the modulators include known basal media optionally supplemented with protein components, particularly serum, e.g., fetal or new-born calf serum. Exemplary media include Eagle's Basal Medium; Eagle's Minimal Essential Medium; Dulbecco's Modified Eagle's Medium; Ham's Media, e.g., F10 Medium; F12 medium; Puck's N15 Medium, Puck's N16 Medium; Waymoth's MB 7521 Medium; McCoy's 5A Medium; RPMI Media 1603, 1634, and 1640; Leibovitz's L15 Medium; ATCC (American Type Culture Collection) CRCM 30; MCDB Media 101, 102, 103, 104; CMRL Media 1066, 1415, 1066, 1415; and Hank's or Earl's Balanced Salt Solution. The basal medium employed, as known in the art, contains nutrients essential for supporting growth of the cell under culture, commonly including essential amino acids, fatty acids, and carbohydrates. The media typically include additional essential ingredients such as vitamins, cofactors, trace elements, and salts in assimilable quantities. Other biological compounds necessary for the survival/function of the particular cells, such as hormones and antibiotics are also typically included. The media also generally include buffers, pH adjusters, pH indicators, and the like.

Media containing the modulators are applicable to a variety of cells, especially eukaryotic cells. The media are suitable for culturing animal cells, specifically mammalian cells and especially human cells. Specific cell types useful for culture in the processes of the invention accordingly include: cells derived from mammalian tissues, organs and glands such as the brain, heart, lung, stomach, intestines, thyroid, adrenal, thymus, parathyroid, testes, liver, kidney, bladder, spleen, pancreas, gall bladder, ovaries, uterus, prostate, and skin; reproductive cells (sperm and ova); lymph nodes, bone, cartilage, and interstitial cells; blood cells including immunocytes, cytophages such as macrophages, lymphocytes, leukocytes, erythrocytes, and platelets.

Culture techniques useful in conjunction with the modulators include the use of solid supports, (especially for anchorage-dependent cells in, for example, monolayer or suspension culture) such as glass, carbon, cellulose, hollow fiber membranes, suspendable particulate membranes, and solid substrate forms, such as agarose gels, wherein the compound is caged within the bead, trapped within the matrix, or covalently attached, i.e. as a mixed disulfide. The modulators are useful in primary cultures; serial cultures; subcultures; preservation of cultures, such as frozen or dried cultures; and encapsulated cells; cultures also may be transferred from conventional media to media containing the modulators by known transfer techniques.

As a general guideline for effective concentrations of modulator for treating neoplasia, from about 0.01 fg to 100 ng vitaletheine modulator(s) per milliliter culture, and preferably from about 0.1 to 10,000 fg vitaletheine modulator(s) per milliliter culture is recommended, or for in vivo applications from about 0.1 fg to 1,000 ng vitaletheine modulator(s) per kg body weight, and preferably from about 1 fg to 10 ng vitaletheine modulator(s) per kg body weight is recommended, depending particularly on the potency of the modulator and cell densities. When combinations of the modulators are employed, total amount of modulator will usually be within these ranges. Since the effective amount at the lower concentrations of vitaletheine modulator(s) recited approaches one molecule of modulator per cell, it is especially important to adjust the concentration of modulator at the lower end of these ranges according to the number of cells present in culture or in vivo, i.e., the target cell density, such as the density of leukemia cells, as readily determined by standard methods. Most preferably, the basal culture medium employed is supplemented with sufficient modulator to provide a total concentration of modulator(s) in the medium of from about 1 to 2 fg modulator per milliliter of medium, again depending primarily upon the potency of the modulator, the type of cell, and upon target cell densities. Likewise, for in vivo applications total concentration of modulator(s) is most preferably from 10 fg to 100 pg/kg depending upon the potency of the modulator, the type of cell, and upon target cell densities. Typically, the above concentration ranges of modulator(s) will comprise effective amounts of modulator for cultures irrespective of cell densities, but special problems of nutrient and modulator supply and waste removal exist in confluent cultures. Consequently, confluent cultures should be avoided when possible unless special provisions are made for these environmental needs. Up to ten million cells per milliliter culture is a useful range. of cell concentration, for confluency increases at higher cellular densities, again depending upon the size of the cells. Typical cell densities comprise from about one hundred thousand to ten million cells per milliliter culture, and the above described dosages are based upon such densities. Since the effective concentration of modulator has approached one molecule per cell, the concentration of modulator is varied as the concentration of cells increases or decreases.

Replenishment of the vitaletheine modulator(s) to regulate biological activity as desired may be advisable. Diurnal variations in enzymatic activity are notable, and diurnal or 48 hour replacement is generally recommended, typically depending upon the stability of a particular vitaletheine modulator(s) in the particular environment and the particular type of cell targeted.

The method of the invention is useful for reducing in vivo both solid (non-hematolymphoid) and soft (hematolymphoid) tumor burden, particularly in mammals, and inhibiting intra-vascularization of tumor cells, especially cells of metastasizing tumors. The compounds are thus broadly useful for reducing tumor burden, by inhibiting tumor growth or by inhibiting tumor metastasis, or both. In particular, they are contemplated to be effective either alone or in combination with β-alethine or other metabolites or inhibitors of their metabolism, against a broad spectrum of malignant tumors, especially tumors such as melanomas; myelomas; lymphomas; leukemias; and carcinomas; including ovarian tumors; cervical tumors; uterine tumors; breast tumors; long tumors (small cell and non-cell carcinomas); colon and stomach tumors; hepatocellular tumors; pancreas, midgut, liver, bone, bladder, and prostate tumors; brain tumors (primary and secondary); larynx and oral cavity tumors; skin tumors; and Hodgkin's disease. The modulators are contemplated as useful inter alia in the treatment of neoplasia 1) prophylactically; 2) as a primary therapy for inhibiting tumor growth, particularly that of slowly-growing tumors; and 3) as a supplemental therapy pursuant to surgical intervention for removal or debulking of tumors, particularly virulent or primary tumors. Treatment with the modulators has been found to inhibit development of aggressive tumors, diminish tumor mass, regress tumors, and inhibit tumor metastasis. It is recommended that anti-tumor therapy commence at the earliest tumor stage possible, particularly to avoid peripheral physiological complications caused by the presence or metastasis of large tumors, and to diminish the systemic burden of tumor debri subsequent to the implementation of an effective regimen.

Based on illustrated and non-illustrated research data, it appears that neoplasia to be treated according to the invention may demonstrate an inherent resistance to extra-biological amounts of vitaletheine modulator(s), in vitro or in vivo. This is overcome as concentration(s) are increased at a dosage at which a response is first observed$ herein referred to as "threshold dosage". The response augments rapidly with dose to a maximum response at a dosage herein referred to as "optimum dosage"; beyond this point, the therapeutic response typically declines with increasing dose to that observed prior to the exposure. The dosage at which basal biological activity is restored is referred to herein as "endpoint dosage". The dosage providing a response from between about the threshold dosage and the endpoint dosage is referred to herein as the "effective concentration or dosage" of the modulator. For example, polymerization of the vitaletheine, in vivo or in vitro, to vitaletheine $V_4$ at dosages above the optimum dosage may result in a decline in the desired response, and may additionally cause proliferation at concentrations greater than the endpoint dosage.

Guidelines for the development of dose-response curves for a particular application are conveniently developed as follows:

DOSE RESPONSE CURVE DEVELOPMENT GUIDELINES

A. Employing Vitaletheine Modulator(s), in vitro

Targeted cells according to the invention are first grown in a modulator-free control or basal culture medium according to standard practice to measure tumor cytotoxicity. Samples of the same cell type at chronologically identical stages of development are then cultured in the same medium according to the invention containing a modulator in the amounts ranging for example from about 0.01 femtograms vitaletheine modulator(s) per milliliter to about 1 microgram vitaletheine modulator(s) per milliliter culture medium, based on exemplary cell densities of about one million cells per milliliter culture; preferably, doses of the compound in $\log_{(10)}$ increments are used to localize the effective concentration of any particular vitaletheine modulator. The cultures are then reexamined over a range flanking the effective dosage in less than one $\log_{(10)}$ increments to thoroughly define the effective concentration, the threshold dosage, and the endpoint dosage for that particular culture. Once the in vitro treatment is optimized, the cells are reinjected to inhibit or regress tumor as determined by standard methods such as palpation, enzyme or specific protein assay, or magnetic resonance or other imaging procedures.

B. Employing Vitaletheine Modulator(s) in in vivo applications

Preferably, the biological activity of the modulator to be employed is evaluated by standard procedures using a control group to establish the basal biological activities under conditions identical to the evaluation of modulated activities. Modulators are administered by routes previously described while the control or basal group receives only the vehicle for administration. For example, groups of 5 or more animals are treated with $\log_{(10)}$ increments of from 0.1 fg to 1,000 ng vitaletheine modulator(s)/kg body weight (such as by i.p. injection in saline, optionally including inhibitors of the metabolism of the modulator(s)), periodically throughout the study, such as three times per week. Tumor samples or measurements are obtained and preserved as the regimen is continued for at least about two weeks and preferably for about 15 weeks or more. After compilation of the data, the response is evaluated graphically with a three-dimensional surface in which the X, Y, and Z axes are dose, week, and response, respectively. The optimum concentration of modulator is easily identified in this manner as a depression in the surface when Z is tumor development. When an inhibitor(s) of metabolism has been included, the optimum dosage of the compound is determined, then the study is repeated holding this concentration of the compound constant and varying the concentration of the inhibitor(s) to optimize the inhibitor(s) concentration(s) as well. Repeating the analysis with more closely spaced increments of modulator, for example half $\log_{(10)}$, and with a constant optimal dose of inhibitor, then, localizes the optimum and effective range of concentrations for the compounds. Therapeutic effects are expected with as little as 100 ng of inhibitor/kg body weight and with less than 100 pg vitaletheine modulator/kg body weight.

EXAMPLES

Example I. Synthesis of N,N'-bis-(CBZ)-β-alethine {S,S'-Bis[(N-carbobenzoxy-β-alanyl)-2-aminoethyl] Disulfide}

A solution of dicyclohexylcarbodiimide (23.3 g) was added to a solution of N-CBZ-β-alanine (24.84 g) and N-hydroxy-succinimide (12.92 g) in a total volume of about 500 ml of dry 10% acetonitrile in dichloromethane. Dicyclohexylurea (24.51 g) precipitated as a by-product upon formation of the active ester. The active ester was dried to an oil and triturated with anhydrous ethyl ether. The precipitate was resuspended in dichloromethane and additional dicyclohexylurea was allowed to precipitate. The resulting dichloromethane solution of active ester was filtered and added to a previously prepared solution of cystamine (8.5 g). The desired product, N,N'-bis-(CBZ)-β-alethine precipitated from this mixture. The mother liquor, anhydrous ether and dichloromethane extracts of the product, and the anhydrous ether extract of the active ester, above, were dried and recombined to augment the yield of product. N,N'-bis-(CBZ)-β-alethine was practically insoluble in water, hot ethyl acetate, and hot ether, and these were used to further extract impurities. The product was recrystallized from dimethyl sulfoxide with acetonitrile (or water), and again rinsed with ethyl acetate and ether. This last process resulted in a 1° C. increase in melting point to 180°–181° C. (uncorrected). Yields of N,N'-bis-(CBZ)-β-alethine of 85–90% were routinely obtained, and near-quantitative yields are possible. When dried over $P_2O_5$, in vacuo, the product appeared to retain one mole equivalent of water, and was analyzed according as the monohydrate.

Anal. Calcd. for $C_{26}H_{34}N_4O_6S_2 \cdot H_2O$: C, 53.78; H, 6.25; N, 9.65. Found: C, 54.23; H, 6.56; N, 9.66. Sample analyzed by Ruby Ju, Department of Chemistry, University of New Mexico, Albuquerque, N.M.

Example II. Synthesis and Characterization of the Benzyl Derivative of Vitaletheine

A. Synthesis

The following reagents were added with mixing in the order listed to an Erlenmeyer flask (500 ml): N,N'-bis-(carbobenzoxy)-$\beta$-alethine (0.76 g) from Example I, above, dimethyl sulfoxide (0.75 ml), N,N'-dimethylformamide (0.75 ml), pyridine (1 ml), chloroform (21 ml), water (150 ml), and iodine (3.3 g). Upon addition of the iodine the pH began to decrease, and was maintained at 5.7 by slowly adding zinc oxide (0.3 to 0.4 g). It was desirable to maintain this slightly acidic pH to optimize reaction rates. This mixture allowed controlled reaction, continuous extraction of the intermediate product from the organic reagent phase into the aqueous phase, and continuous monitoring of the pH of the aqueous phase. When the reaction began to subside, which was indicated by a stabilization of pH, the aqueous phase was removed and subjected to repeated extractions with chloroform until no color was evident in the organic phase. Periodically during these extractions, the pH was readjusted to 6.0 with a minimum amount of ZnO. When completely extracted and neutralized to pH 6.0, the aqueous phase was dried on a rotoevaporator at low temperature (<40° C.) to a viscous oil. During this process, the organic phase of the reaction mixture was reextracted with water to recover residual intermediate product, which was subsequently extracted with chloroform, neutralized with ZnO, and dried with the first aqueous extract.

This stage in the synthesis represents a branch point for the synthesis of the desired compound; at this point, either the desired compound or the benzyl derivative thereof can be obtained. For example, either vitaletheine $V_4$ (Example III and Formula IX) or the benzyl derivative of vitaletheine of the Formula VIII can be produced at this stage.

To obtain the benzyl derivative of vitaletheine, the aqueous extracts obtained as above were treated with ten volumes of acetonitrile to precipitate the benzyl derivative as the primary product.

B. Characterization of the Benzyl Derivative of Vitaletheine

The benzyl derivative obtained above had approximately the same molecular weight as the blocked alethine starting material. However the derivative was unlike N,N'-bis-(CBZ)-$\beta$-alethine in many respects: it was soluble in water; it had unique [$^{13}$C]— and [$^{1}$H]-NMR spectra; and its IR spectrum was likewise distinct. The benzyl derivative was purified as the calcium salt, but this difference from the zinc salt of vitaletheine $V_4$ (below) could not account for the extremely high melting point of the former; the benzyl derivative melted at temperatures in excess of 300° C., while the starting material melted at 180°–181° C. (uncorrected). The NMR spectra of the zinc and calcium salts of the benzyl derivative were quite similar, evidence that salts alone could not account for these differences.

The spectra of the benzyl derivative were not consistent with thiazolidine or cyclic-urethane structures, and no detectable disulfide or thiol was present, suggesting that like vitaletheine $V_4$, the benzyl derivative was formed by the nucleophilic attack involving sulfur on one of the carbonyl carbons in each monomer. Unlike vitaletheine $V_4$, the predominant polymer in the product benzyl derivative was identified as a dimer, probably formed by attacks of each monomer on the carbonyl carbon of the other, as described above. The quaternary carbons preset appeared identical, and were not shifted upfield (**) in the NMR spectrum, in contrast to the pronounced upfield shift of the quaternary carbon atoms present in the vitaletheine tetramer, indicating fewer structural constraints in the benzyl derivative dimer than in the vitaletheine tetramer. Elemental analysis indicated additional material had crystallized with the benzyl derivative, and good correlation was found for inclusion in the dimer of 2 mole equivalents of calcium ion and one mole equivalent of oxygen per mole of the dimer. This was consistent with the presence of a calcium oxide bridge between two dimers, stabilized by hydrogen bonding. The following was the result of elemental analysis for the benzyl derivative obtained above, correcting for the presence of the calculated oxygen and calcium ion:

Anal. Calcd. for $C_{26}H_{34}N_4O_8S_2 \cdot 2Ca^{++} \cdot O^=$: C, 45.20; H, 4.96; N, 8.11. Found: C, 44.97; H, 4.98; N, 8.04. Sample analyzed by Ruby Ju, Department of Chemistry, University of New Mexico, Albuquerque, N.M.

Example III. Synthesis and Characterization of Vitaletheine $V_4$

A. Synthesis

The benzyl group was removed by repeatedly exposing the dried aqueous extracts obtained in Example IIA to ultraviolet light (Pen-ray quartz lamp, Ultra Violet Products, Inc., Cambridge, U.K.) and extracting with chloroform until no color developed under UV irradiation, and no color was extractable into chloroform. UV irradiation is particularly recommended for effectively obtaining product substantially devoid of aromatic moieties, without causing more serious and inactivating rearrangements and decompositions, as described previously. The product (when completely free of aromatics) was dried, neutralized in water with ZnO, and recrystallized from dimethylsulfoxide with acetonitrile to yield the zinc salt of vitaletheine $V_4$.

Characterization of Vitaletheine $V_4$

Vitaletheine $V_4$ was likewise distinct with reference to both the starting material and the benzyl derivative. Obtained in greater than 50% yield from the above procedure, it melted with decomposition at 233°–235° C. (uncorrected). Evolution of gas signified decomposition of the molecule; the evolved gas ($CO_2$) was trapped by bubbling through a saturated solution of $Ba(OH)_2$ under $N_2$, with recovery of $BaCO_3$. Decomposition of the molecule on heating was consistent with the presumptive thermal lability of the postulated carboxyamino structure, as was the evolution of $CO_2$ upon heating, and the recovery of the trapped $CO_2$ as the insoluble barium carbonate. The possibility that the evolved gas resulted from decomposition of zinc carbonate contaminating the vitaletheine $V_4$ was deemed unlikely, since this salt decomposes with $CO_2$ evolution at 300° C. The spectral evidence likewise indicated a structure unique to vitaletheine $V_4$, comprising covalent attachment of the carbon in question (2) to the $\beta$-aletheine moiety. Concomitant with the evolution of $CO_2$, losses of a sharp N—H stretch resonance at 3290 cm$^{-1}$ and other resonances associated with the carboxyamino structure were observed in the IR spectra.

Vitaletheine $V_4$ as prepared was somewhat hygroscopic, possibly exacerbated by residual dimethylsulfoxide. The following elemental analysis reflected the propensity of the molecule to gain water:

Anal. Calcd. for $C_{24}H_{44}N_8O_{12}S_4.2\ Zn^{++}.8\ H_2O$: C, 27.72; H, 5.82; N, 10.78. Found: C, 28.56; H, 5.94; N, 10.96. Sample analyzed by Ruby Ju, Department of Chemistry, University of New Mexico, Albuquerque, N.M.

The results of several different analyses indicated that the vitaletheine dimer contained 1 $Zn^{+2}$, the trimer contained 1.5 $Zn^{+2}$, and the tetramer contained 2 $Zn^{+2}$ per mole of polymer.

Example IV. Synthesis and Characterization of Vitalethine via β-alethine

A. Synthesis of β-alethine.2HCl or N,N'-bis-(β-alanyl)-cystamine or N,N'-bis-(β-alanyl-2-aminoethyl) disulfide Complete removal of the carbobenzoxy group was accomplished according to procedures described in *J. Am. Chem. Soc.* 86: 1202–1206 (1964), incorporated herein by reference. After deblocking with four equivalents of hydrogen bromide in glacial acetic acid per mole of the N,N'-bis-(CBZ)-β-alethine (from Example I, above) for 15 hours, the β-alethine was purified by precipitating with acetonitrile, rinsing with anhydrous ethyl ether, resuspension in water and filtering, and precipitating the mixed salts with acetonitrile. Initial yields were in excess of 80% theoretical. The β-alethine was converted to the hydrochloride salt by passing the preparation over a 30 ml×15 cm long column of Dowex AG 1X8 (chloride form) (Dow Chemical Corp., Midland, Mich., U.S.A.) which had been previously prepared by eluting with 1M potassium chloride and rinsing thoroughly with DI (deionized) water. Neutralization with $Ca(OH)_2$ and recrystallization of the β-alethine hydrochloride from water with acetonitrile resulted in fine needles which melted at 224°–225° C. (uncorrected).

Anal. Calcd. for $C_{10}H_{22}N_4O_2S_2.2HCl$: C, 32.69; H, 6.59; N, 15.25. Found: C, 32.52; H, 6.69; N, 15.32. Sample analyzed by Ruby Ju, Department of Chemistry, University of New Mexico, Albuquerque, N.M.

B. Synthesis of Vitalethine

To a suspension of ZnO (6.5 mg from King's Specialty Company, Fort Wayne, Ind. U.S.A.) and β-alethine (6.35 mg from Example IV. A. above) in pyridine (12.6 mg from Fisher Scientific, Fair Lawn, N.J., U.S.A.) and dimethylsulfoxide (0.5 ml from Sigma Chemical Company, St. Louis, Mo., U.S.A.), and in a vessel equipped with a gas trap containing sodium hydroxide (at least 1M), was added 0.2 ml of a solution of phosgene (20% in toluene from Fluka Chemical Corp. Ronkonkoma, N.Y., U.S.A.). Packing of the reaction vessel in dry ice controls the exothermic reaction and improves the yields of large-scale preparations. After 48 hours of reaction the excess phosgene was blown into the alkali trap with $N_2$. The product was precipitated in the vessel with acetonitrile (approximately 50 ml from Fisher Scientific, Fair Lawn, N.J., U.S.A.). Vitalethine can be recrystallized from water with acetonitrile.

C. Characterization of Vitalethine

Unlike the starting material, β-alethine which melted at 224°–225° C. (uncorrected), the vitalethine powder sintered and turned brown at 215°–220° C., but did not melt until 242° C. (uncorrected) at which point obvious decomposition and evolution of gas occurred. This behavior resembled that of vitaletheine $V_4$, in that gas was also evolved upon melting of the polymer. The infrared spectrum of the two compounds were likewise similar, but the vitalethine spectrum did not exhibit the C—O stretch bands observed in the polymer. Both compounds lost infrared resonances associated with the carboxy-amino group upon thermally labilizing this moiety. This was particularly true of vitalethine, for major peaks disappeared at 1600 and 1455 $cm^{-1}$ (resonances for the ionized carboxylic moiety), and losses in the fine structure in the region 2800 to 3300 $cm^{-1}$ and 900 to 1360 $cm^{-1}$ (i.e., those associated with the N—H and C—N moieties of the carboxy-amino group) were also apparent upon heating at 242° C.

|  | a<br>S—$CH_2$ | b<br>$CH_2$—N | c<br>H—N—C=O | d<br>O=C—$CH_2$ | e<br>$CH_2$—N | f<br>H—N—C=O<br>\\<br>$O^-$ |
|---|---|---|---|---|---|---|
| [$^{13}C$]-NMR | | | | | | |
| β-alethine | 37.59 | 39.04 | 172.79 | 32.9 | 36.71 | |
| Vitaletheine | | | | | | |
| $V_4$ | 36.66 | 35.93 | 47.06*44.75<br>39.41*38.51 | 50.39 | 32.96 | 172.73 |
| Benzyl derivative | 33.79 | 35.76 | 156.46** | 48.36 | 34.67 | 172.25 |
| [$^1H$]-NMR | | | | | | |
| β-alethine* | 2.524 | 3.094 | | 2.694 | 3.367 | |
| β-aletheine ($Zn^{++}$) | 2.512 | 3.084 | | 2.695 | 3.372 | |
| β-aletheine (+$I_2$) | 2.512 | 3.087 | | 2.687 | 3.366 | |
| Vitaletheine | | | | | | |
| $V_4$ ($D_2O$) | 2.502 | 3.081 | | 2.937 | 3.416 | |
| (DMSO-$D_6$) | 2.200 | 2.763 | 7.84 | 2.418 | 3.131 | 7.38 |
| Benzyl derivative | | | | | | |
| ($D_2O$) | 2.232 | 3.201 | | 2.841 | 3.330 | |
| (DMSO-$D_6$) | 2.210 | 3.176 | 7.84 | 2.593 | 3.309 | 7.247 |
| bis-(CBZ)-β-alethine | | | | | | |
| (DMSO-$D_6$) | 2.740 | 3.309 | 8.085 | 2.254 | 3.192 | 7.24 |
| Reductase Factor (Inactive) | 2.71 | 3.08 | | 2.90 | 3.28 | |

-continued

| | a<br>S—$CH_2$ | b<br>$CH_2$—N | c<br>H—N—C=O | d<br>O=C—$CH_2$ | e<br>$CH_2$—N |
|---|---|---|---|---|---|

$$\text{H—N—C}\begin{array}{c}\diagup O^-\\=O\end{array}\text{ f}$$

IR (cm$^{-1}$)

$$\text{f}$$
$$\text{H—N—C}\begin{array}{c}=O\\\diagdown O^-\end{array}$$

| | | | | |
|---|---|---|---|---|
| Vitalethine | | 3170w | | 3290m |
| | | 1550w | | 1560s |
| | | | | 1600m |
| | | | | 1455s |
| Vitaletheine | | | | |
| $V_4$ | 710w | 3080s | | 3290s |
| | | 1530m | | 1560s |
| | | | | 1253m |
| | | | | 1650s |
| | | | | 956m |
| Benzyl derivative | 692–570w | 3308s | | 3308s |
| | | 1542s | | 1542s |
| | | 1635s | | 1253m |
| | | | | 1684s |
| bis-(CBZ)-β-alethine | | 3345s | | 3345s |
| | | 1545m | | 1535s |
| | | 1640s | | 1270m |
| | | | | 1682s |

$$\begin{array}{c}\text{f}\\-\text{N—H}\end{array}$$

| | | | | |
|---|---|---|---|---|
| β-alethine | 660w | 3250w | | 3270v |
| | | 1555w-s | | 2970s-w |
| | | 1286m | | 1462s |
| | | 1620s | | 1620s |
| | | | | 1128s |

*β-alethine was reduced with REDUCTACRYL* (a proprietary reducing agent available from Calbiochem, San Diego, CA, USA) in the presence of ZnO to form β-aletheine. The latter reacted with $I_2$ to provide a third reference compound, probably the sulfenyl iodide.

Vitaletheine $V_4$ and vitalethine were unique in that resonances associated with the moiety "f" above disappeared when the compounds melted and decomposed at 233°–235° C. (uncorrected) and 242° C., respectively, presumably due to loss of $CO_2$. In vitaletheine $V_4$, these losses occurred without concomitant losses in the regions designating a (—C—O—)$_y$ polymer; thus the decarboxylated form of Vitaletheine $V_4$ appeared to be an oligomer of β-aletheine similar to the undecarboxylated polymer, but lacking the carboxy moieties.

Peaks for Vitalethine: 3290m, 3170w with shoulder at 3100, 2990m, 1660s, 1600w, 1565m, 1455s, 1410w with 1400 shoulder, 1330w with 1310 shoulder, 1260m with 1230 shoulder, 1190w, 1135m, 1100m with 1090 shoulder, 1030m-s, 955m.

Peaks for heated Vitalethine: 3120s (broad), 1655s, 1550m, 1405s with shoulders at 1450 and 1390.

The IR spectrum of vitaletheine $V_4$, following, was shifted by exchanging acetonitrile for water of hydration in the complex.

Peaks for Vitaletheine $V_4$: 3290s, 3080s/broad to 2500, 1650s, 1560s, 1530m, 1453w, 1417w, 1393w, 1346w, 1318w, 1253m, 1190s, 1170s, 1115w/shoulder, 1040s, 1030s, 956m, 790m with shoulder, 709w/broad, 612m/sharp, 526m. These shifts approximated those observed in the spectrum of β-alethine upon neutralization, below.

β-alethine was unusual in that changes in pH, i.e., neutralization with $Ca(OH)_2$, caused pronounced shifts in the positions and intensities of bands.

Peaks (HCl salt): 3270s, 3170s, 2970s, 2700w, 2550w, 2020w, 1657s, 1595m, 1560s, 1450s, 1409m, 1390w, 1354w, 1325m, 1300w, shoulder/1252m/shoulder, 1188m, 1129m, 1097m, 1079w, 1030w, 950w, 905w, 829m.

Peaks (neutralized): 3250w, 3180w, 2940m/broad, 2375s, 2230s, 2157s, 1936w, 1620s, 15552, 1462s, 1432 shoulder, 1400m, 1342m, 1286m, 1217m, 1188m,1128s, 1020m, 810w, 719m, 660w.

The benzyl derivative displayed considerable homology with vitaletheine V4.

Peaks: 3308s, 3060w, 2942w, 1684s, 1635s, 1542s, 1447m, 1380w, 1335w, 1286w, 1253m, 1193s, 1170 shoulder, 1080m, 1040m, 980w, 738m, 692m, 609m, 550w.

Bis-(CBZ)-β-alethine displayed little of the C—O resonances around 1200 observed in vitaletheine $V_4$ and the benzyl derivative.

Peaks: 3345s, 3310s, 1682s, 1640s, 1545m shoulder, 1535s, 1450w, 1427w, 1375w, 1332m, 1270m, 1231m, 1178w, 1120w, 1030m/broad.

In the following Examples, all cells were cultured at about 37° C. for the specified time.

Example VI: Adaptation of Human Natural Killer (NK) Cells to Culture

Human NK cells were purified as described in *J. Exp. Med.* 169: 99–113, 1989. A standard culture medium for the cells was prepared, comprising RPMI 1640 (Rosewell Park Memorial Institute, from Whittaker M. A. Bioproducts, Walkersville, Md., U.S.A.) containing 10% human AB— sera, penicillin (100 U/ml) and streptomycin (100 μg/ml), which served as the control medium. Experimental media were prepared by adding 25 μl/ml of an appropriate aqueous dilution of vitaletheine $V_4$ to obtain the following final concentrations in separate aliquots of medium containing cells otherwise identical with the controls: 0.1 fg/mml, 1 fg/ml, 10 fg/ml, 100 fg/ml, 1 pg/ml, and 10 pg/ml.

Purified cells ($1 \times 10^6$) were seeded and incubated in the control and test media at 37° C. under 5% $CO_2$. Cells were counted, and checked for viability daily by monitoring trypan blue (0.1% in phosphate buffered saline) exclusion, and the media containing the same concentration of vitaletheine $V_4$ were changed every two days to maintain physiological pH and to remove waste products from the cells.

Dramatic stabilization of the NK cell population in culture was observed with vitaletheine $V_4$. By day five, no cells survived in the unsupplemented, i.e., control medium. In media containing vitaletheine $V_4$, 70 to 80% of the cells survived for more than a week. Although the extremes of the effective concentration were not defined in this particular experiment, two doses of vitaletheine $V_4$ were selected for further study.

The results of the viability tests are summarized in Table I, following:

TABLE 1

| Day  | No $V_4$    | 1 fg $V_4$/ml | 1 pg $V_4$/ml |
|------|-------------|---------------|---------------|
| 0    | 98 ± 2      | 98 ± 2        | 99 ± 2        |
| 1    | 96 ± 1.5    | 98 ± 2        | 99 ± 2.5      |
| 2    | 45 ± 1.8    | 97 ± 1.5      | 98 ± 3        |
| 3    | 30 ± 1.5    | 98 ± 2.5      | 98 ± 2        |
| 4    | 15 ± 0.5    | 97 ± 3        | 97 ± 3        |
| 5–20 | 0 ± 0       | 97 ± 3        | 97 ± 3        |

Vitaletheine $V_4$ at concentrations of 1 fg/ml and 1 pg/ml stabilized between 70 and 80% of the cells in culture for an entire month, at which time the cells were frozen for forthcoming functional studies. No cells remained in control cultures, i.e., those lacking vitaletheine $V_4$, by day 6 of the study. Unlike the control cells whose ability to exclude trypan blue dropped precipitously from the first day in culture, 97±3% of the cells in the vitaletheine $V_4$-supplemented media were viable after 30 days in culture, i.e., they excluded the dye.

Example VII: Therapeutic Applications of Vitalethine and Related Compounds in Neoplasia Cloudman S-91 murine melanoma cells (American Type Culture Collection #53.1, Clone M-3) from a C×DBA)F1 male mouse were grown in 75 ml flasks (Corning Glass Works, Corning, N.Y., U.S.A.) containing Ham's F12 medium supplemented with 15% fetal bovine serum, penicillin (100 U/ml), and streptomycin (100 μg/ml), all commercially available from Sigma Chemical Company, St. Louis, Mo., U.S.A. Cultures were incubated at 37° C. under 5.5% carbon dioxide initially at $6 \times 10^6$ cells per ml for two days, with a medium change after one day. Cultures were then trypsinized, split into two fresh flasks at one half the cell density, above, and maintained for one week prior to injection in female (DBA×BALB c) mice (CD2F1/Hsd from Harlan Sprague Dawley, Inc., Indianapolis, Ind., U.S.A.). For injection, cells were first trypsinized, washed 3 times in phosphate buffered saline, and diluted to $1 \times 10^5$ cells/100 μl phosphate buffered saline prior to subcutaneous injection on the rib cage.

The compounds were dissolved in water, filtered through an appropriate sterilizing filter (0.22 μm nonpyrogenac, μ Star LB ™ from Costar ®), diluted to the desired concentration in sterile, physiological saline (0.1 ml), and injected 3 times per week intraperitoneally with a 27 gauge, ⅜ inch allergy syringe (Becton Dickinson, Rutherford, N.J., U.S.A.); by gently lifting the skin on the abdomen and injecting horizontally, puncture of internal organs was avoided, thereby minimizing trauma to the mice.

Definition of several variables affecting tumor growth in these mice was necessary to establish confidence in the tumor model and conclusions therefrom derived. For instance, there was a significant difference in tumor development in old (14 week, bottom curve, FIG. 1) and young mice (4 week, top curve, FIG. 1) injected with physiological saline. Although palpable tumor development was significantly slower in the older mice than the young mice, gross metastasis in the lungs were as pronounced if not more evident in the older mice than in the younger mice. These differences are postulated to be due to age-related differences in growth factors and immune surveillance. Except where specified, mice were matched for age to eliminate this complication in interpreting the results.

Figure 2:
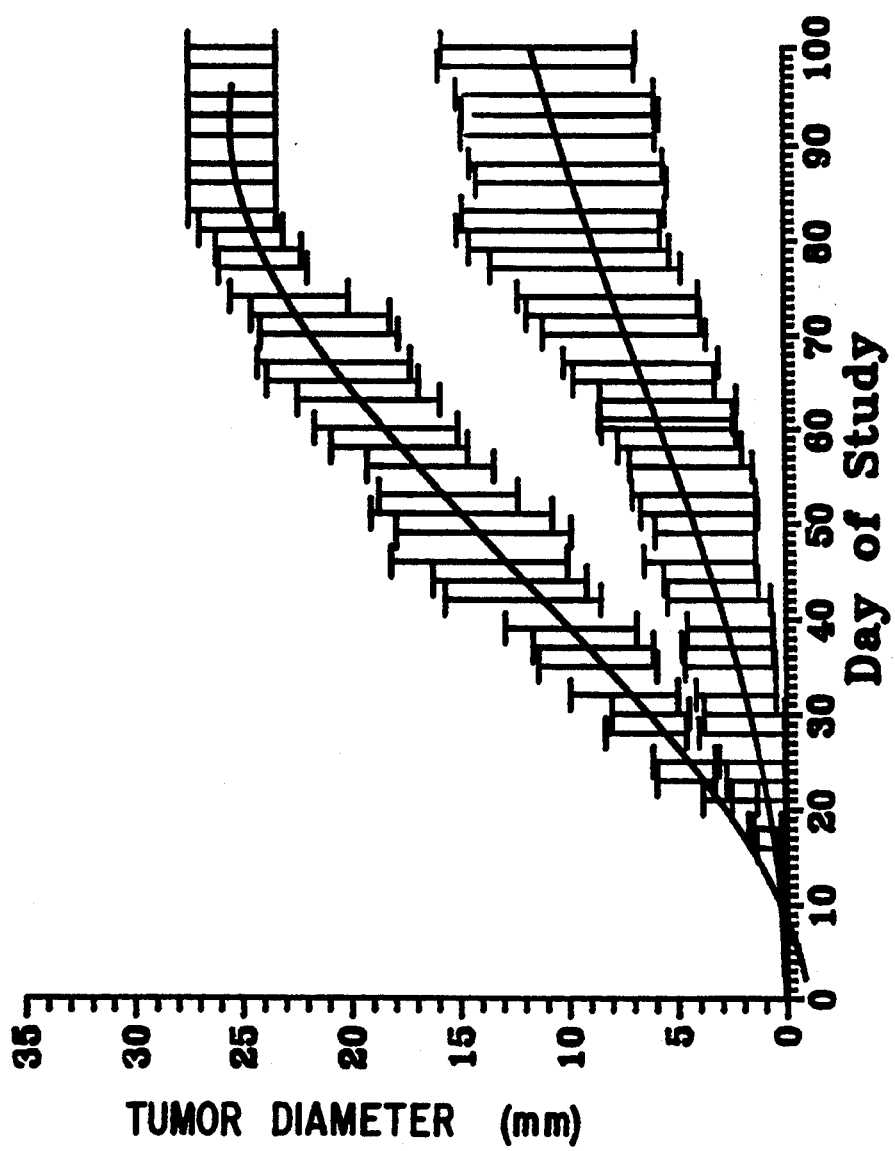
FIG. 2 illustrates the significance of the stimulation in tumor development produced by injections of 100 ng $\beta$-alethine/kg mouse (top curve) relative to saline-injected mice (bottom curve)
Figure 3:
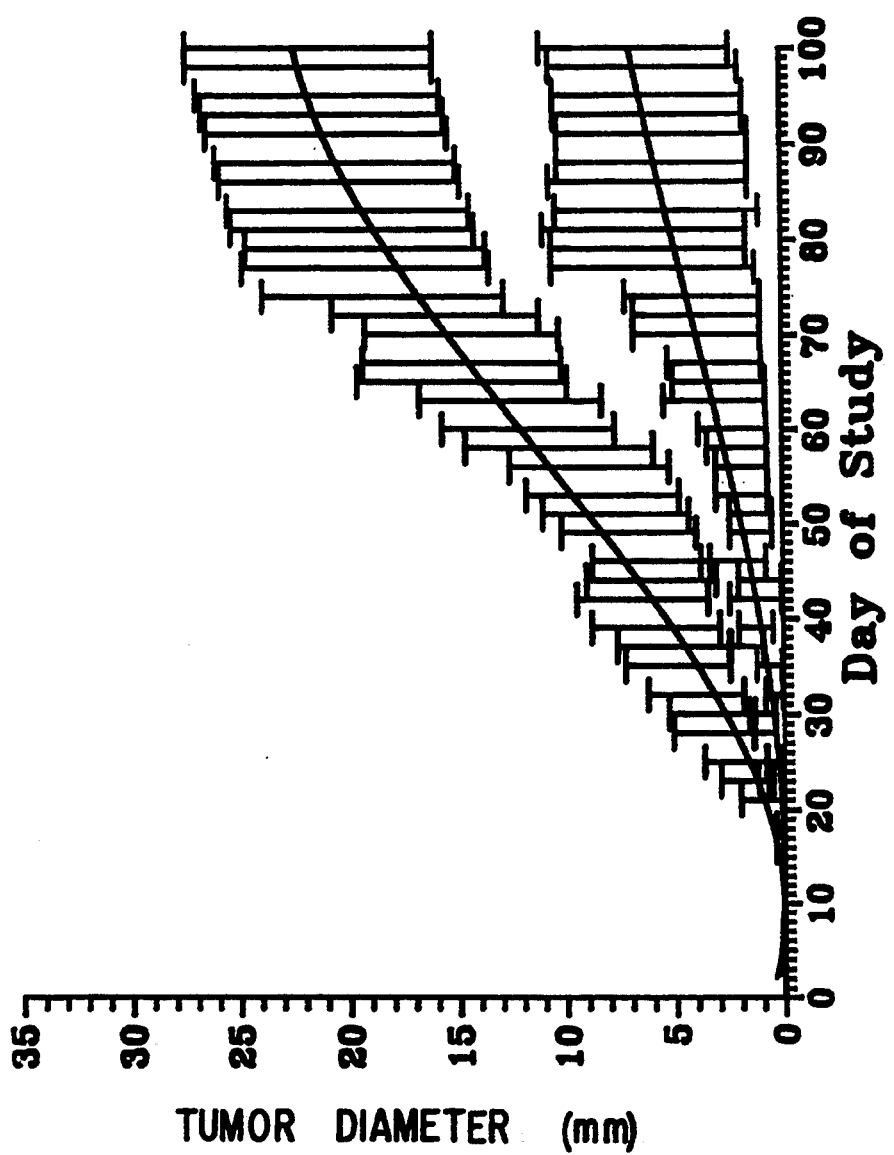
FIG. 3 illustrates the significance of the stimulation in tumor development produced by injections of 100 pg $\beta$-alethine/kg mouse (top curve) relative to mice injected with 100 pg vitalethine/kg body weight.
Figure 4:
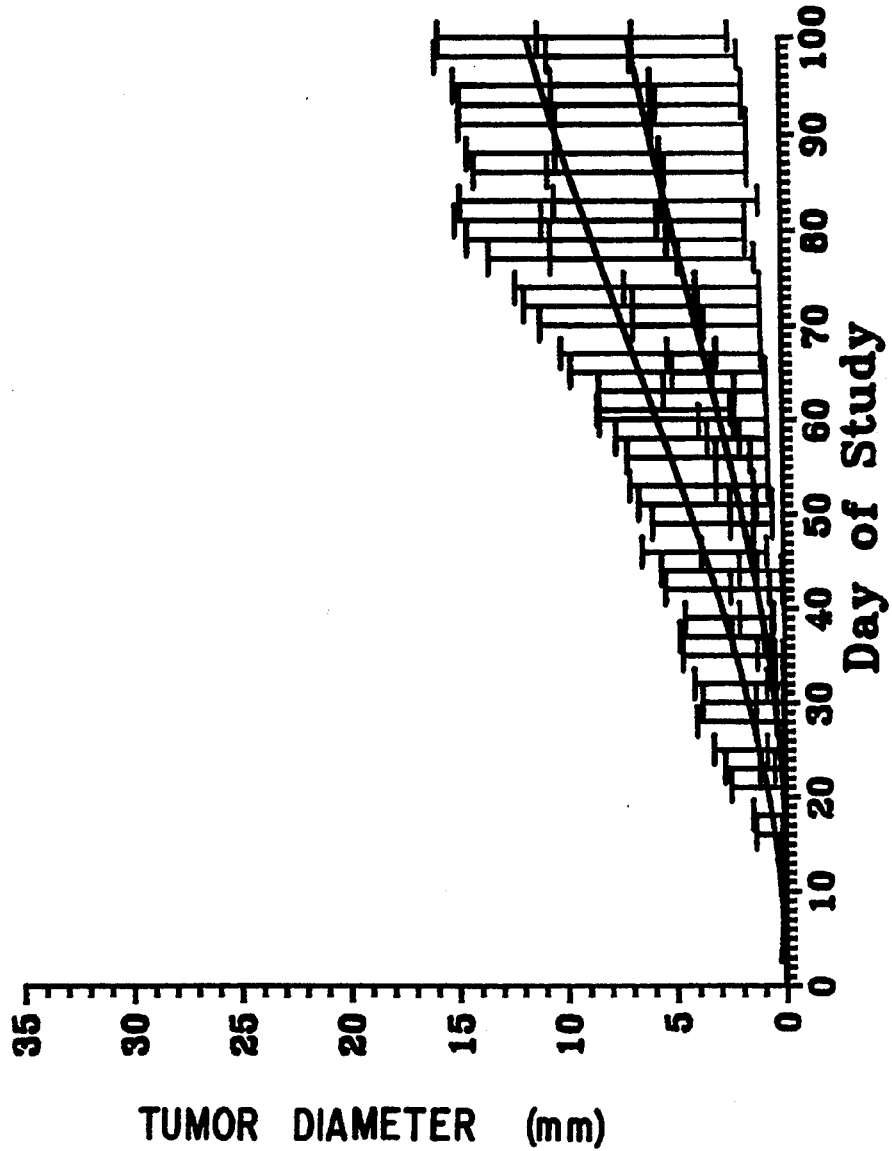
FIG. 4 illustrates the difference between tumor development in control or saline-injected mice (top curve), and vitalethine-injected mice (bottom curve) at nearly the endpoint dosage for vitalethine to maximize detection of impurities, such as underivatized $\beta$-alethine.
Figure 5:
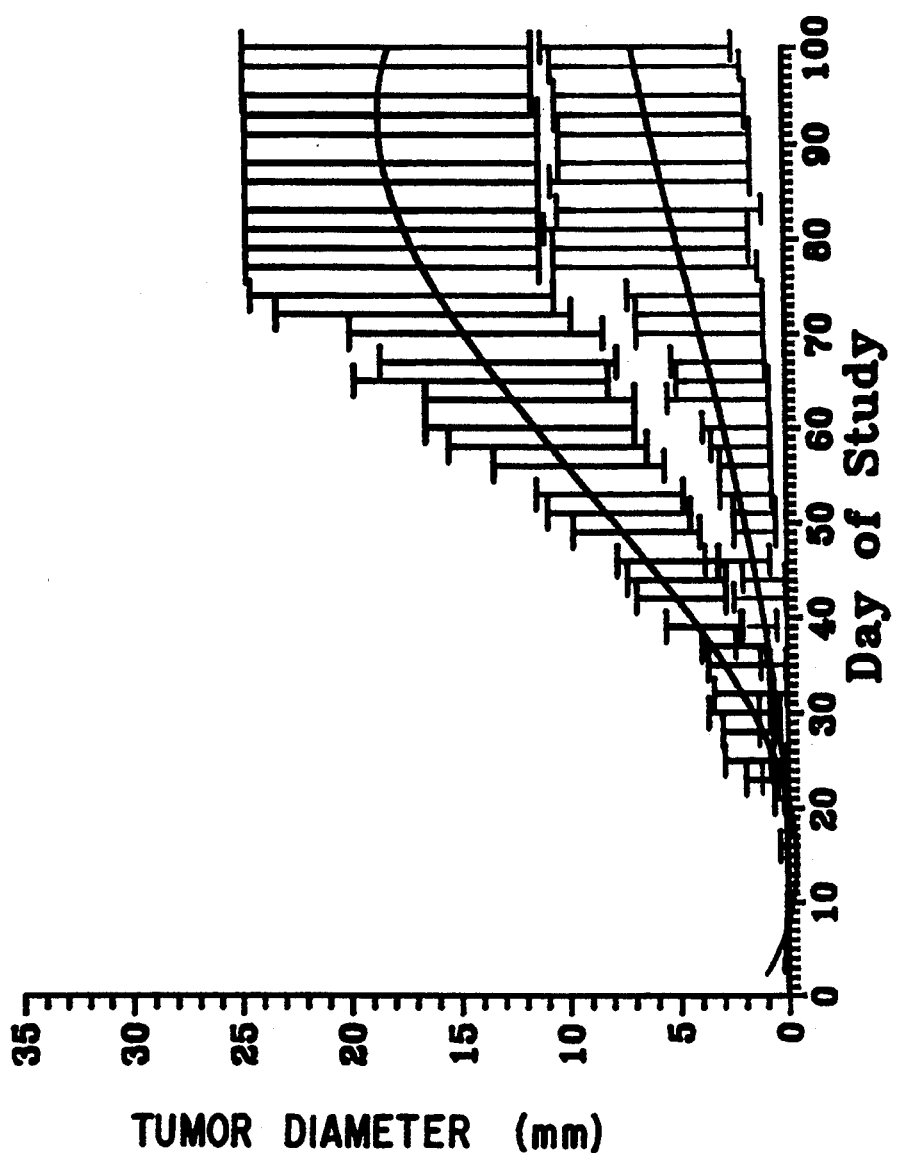
FIG. 5 illustrates the significance of the difference between tumor development in mice injected with the $\beta$-alethine preparation and with the vitalethine preparation at one tenth the relative ratio of compounds illustrated in FIG. 3, and documents the near quantitative conversion of $\beta$-alethine to stable vitalethine by the process of Example IV.
Figure 6:
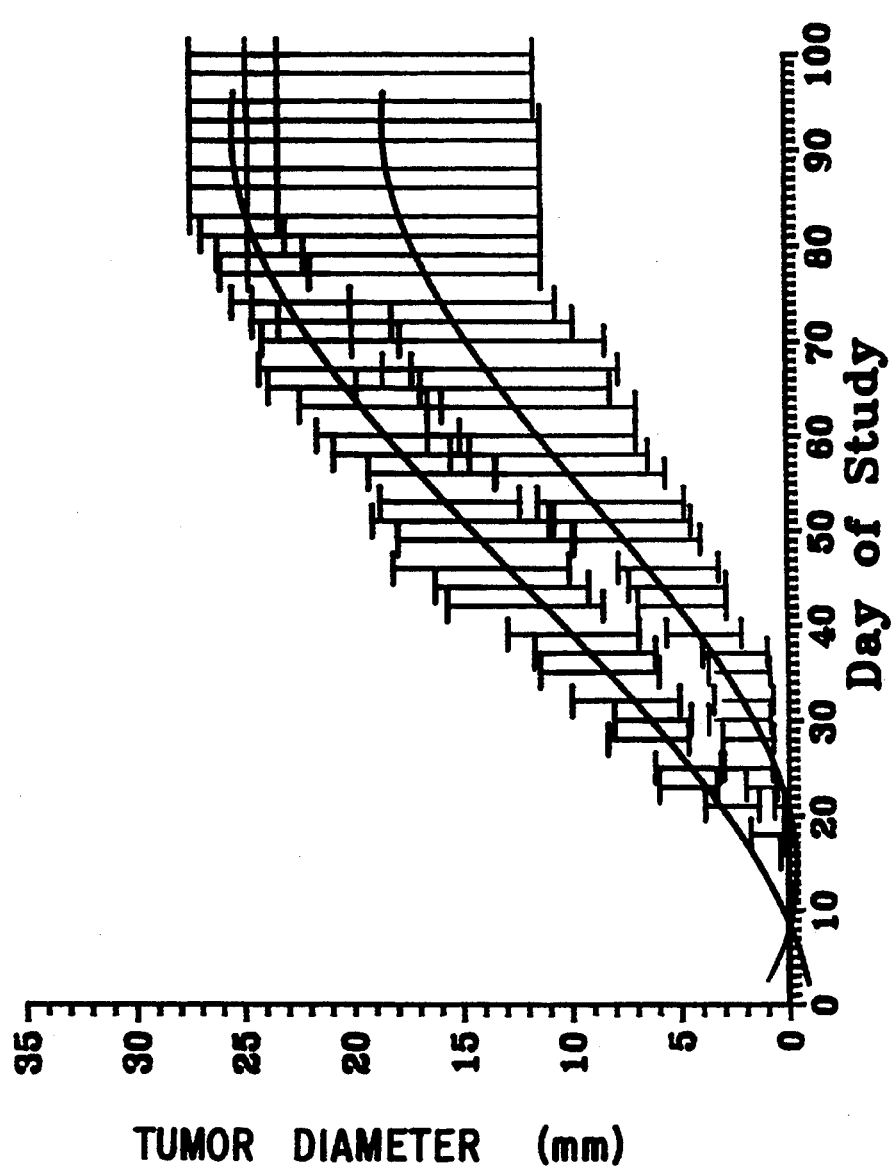
FIG. 6 illustrates the significance of the increase in tumor development in five mice injected with 100 ng $\beta$-alethine/kg mouse (upper curve, and $\log_{(10)}$ pg/kg mouse=5 in FIG. 7) compared to tumor development in five mice injected with 10 pg $\beta$-alethine/kg mouse (lower curve, and $\log_{(10)}$ pg/kg mouse=1 in FIG. 7)
Figure 7:
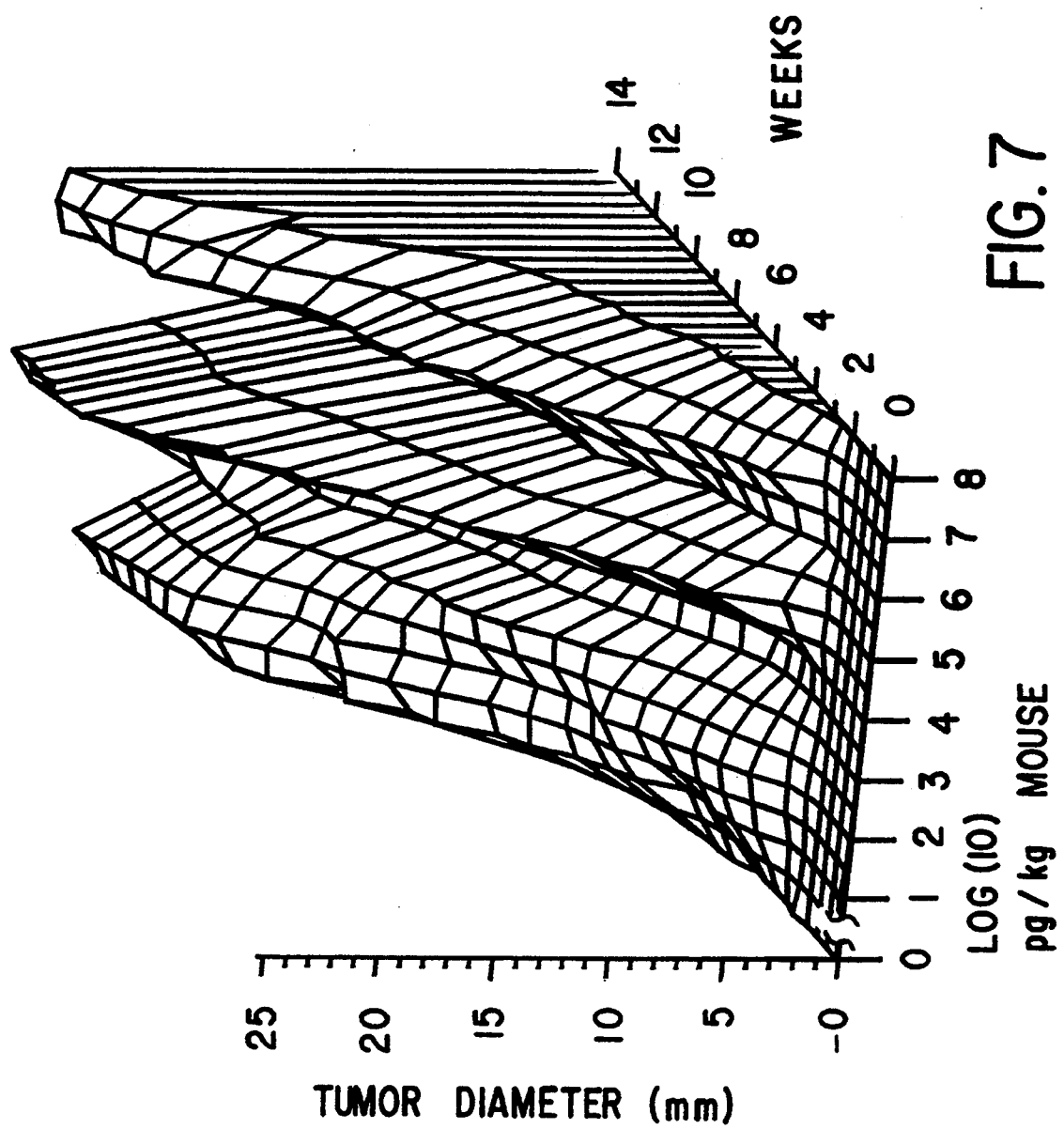
FIG. 7 illustrates average tumor development in five saline-injected mice (0) and in five mice injected with one of eight $\log_{(10)}$ increments of $\beta$-alethine concentrations (from 10 pg/kg mouse to 100 $\mu$g/kg mouse)
Figure 8:
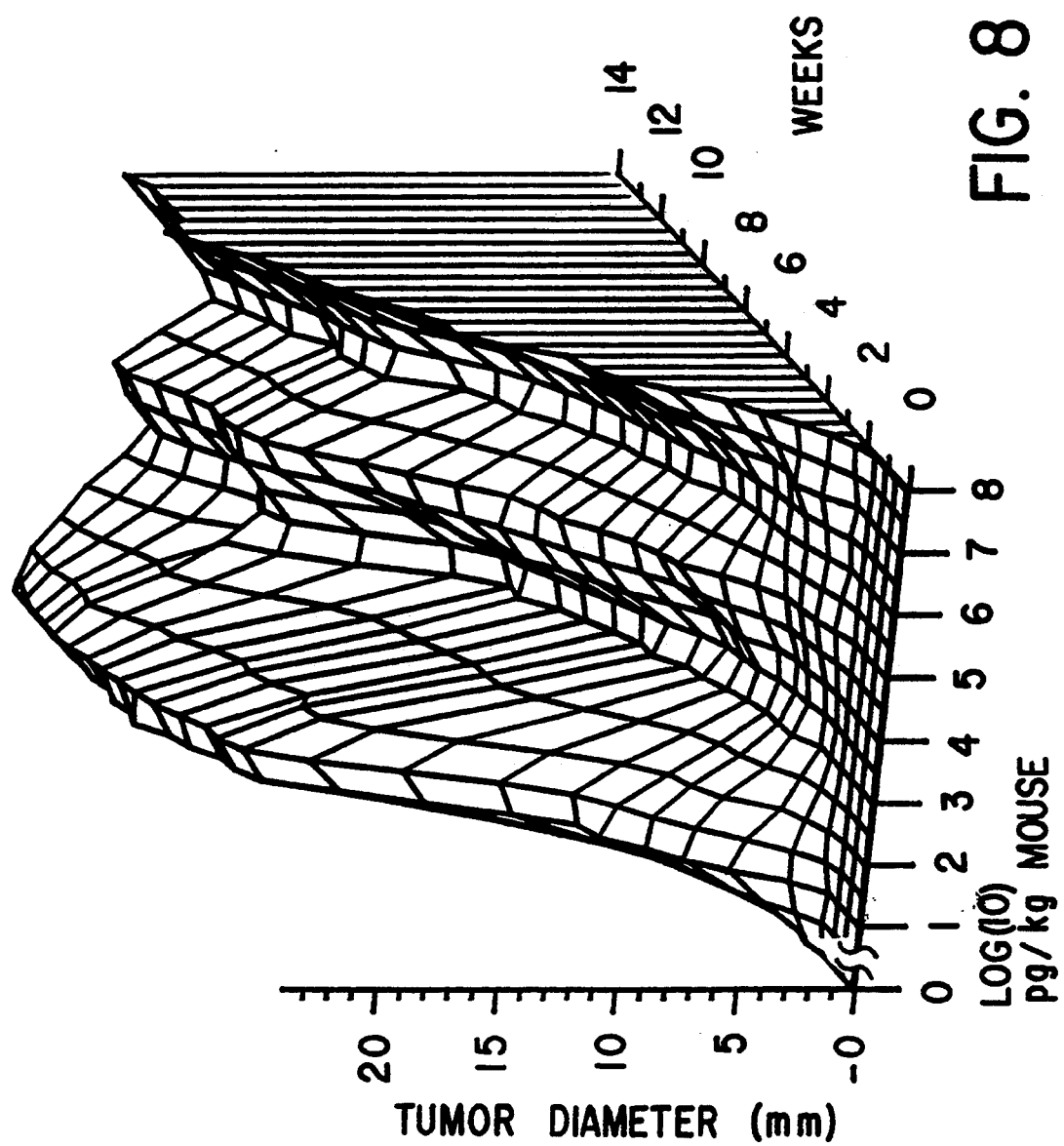
FIG. 8 illustrates average tumor development in five saline-injected mice (0) and in five mice injected with both, one of eight log$_{(10)}$ increments of β-alethine concentrations (from 10 pg/kg mouse to 100 μg/kg mouse) and 1 ng vitaletheine V$_4$/kg mouse.

The compounds administered had to be pure to preclude complications resulting from trace contaminants; this was especially true when the contaminants were among the most potent of the compounds. β-alethine, the immediate precursor of vitalethine in the phosgenation process, caused considerable stimulation of tumor development (FIG. 2), Clearly, contamination of vitalethine with β-alethine could have abrogated any therapeutic effects of the former with the tumor promoting effects of the latter. Phosgenation removes the melanoma promoting properties of the β-alethine preparation almost completely; injections of 100 pg vitalethine/kg mouse produced none of the tumor promotion observed with the same injection dosage of β-alethine (FIG. 3) and, in fact, caused a non-significant decrease in tumor development (FIG. 4). Even at injections of β-alethine one tenth that of vitalethine, significantly greater tumor stimulation was observed with the former than with the latter (FIG. 5). Injections of vitalethine producing a response comparable to that observed that β-alethine were roughly one hundred times higher than the latter (unillustrated data), indicating that phosgenation resulted in at least 99% conversion of β-alethine to vitalethine. Small amounts of β-alethine, resulting from incomplete conversion or from decomposition of the theoretically labile carboxy-amino group, could have been contaminating the preparation of vitalethine. This was of special concern since the tumor-promoting effects of β-alethine were nearly saturated at 10 pg/kg mouse (FIGS. 6 and 7). Furthermore, the oscillation in the response of the tumors to increasing β-alethine concentrations could have made interpretations difficult (FIG. 7). Fortunately, this neoplastic response was both reproducible (FIG. 7 compared to FIG. 8) and interpretable, as described below.

As noted previously, the compounds are effective only at concentrations low with respect to most pharmacological compounds. This raises some interesting theoretical dilemmas. One must assume that the compounds are not metabolized when administered at the low effective dosages, or one must try to retard the degradation of the compounds, for at these concentrations there is essentially no metabolic reserve of the compounds. Clearly, the metabolism of every targeted cell and organ influences the outcome of these considerations; for instance, in cells capable of neither synthesizing nor degrading the compounds, administration of the compounds alone produces the desired result; likewise, in cells in which both degradation and synthesis are favored, administration of only inhibitors of that degradation produces the desired result; in cells incapable of synthesizing the compounds but capable of degrading them, administration of both, inhibitors of their degradation and the compounds themselves, produce optimal results; similarly, in cells in which synthesis is favored but not degradation, no treatment is required. Conceptually, then, one must adjust the environment of the cell to ensure a low steady state concentration of the compounds.

Figure 9:
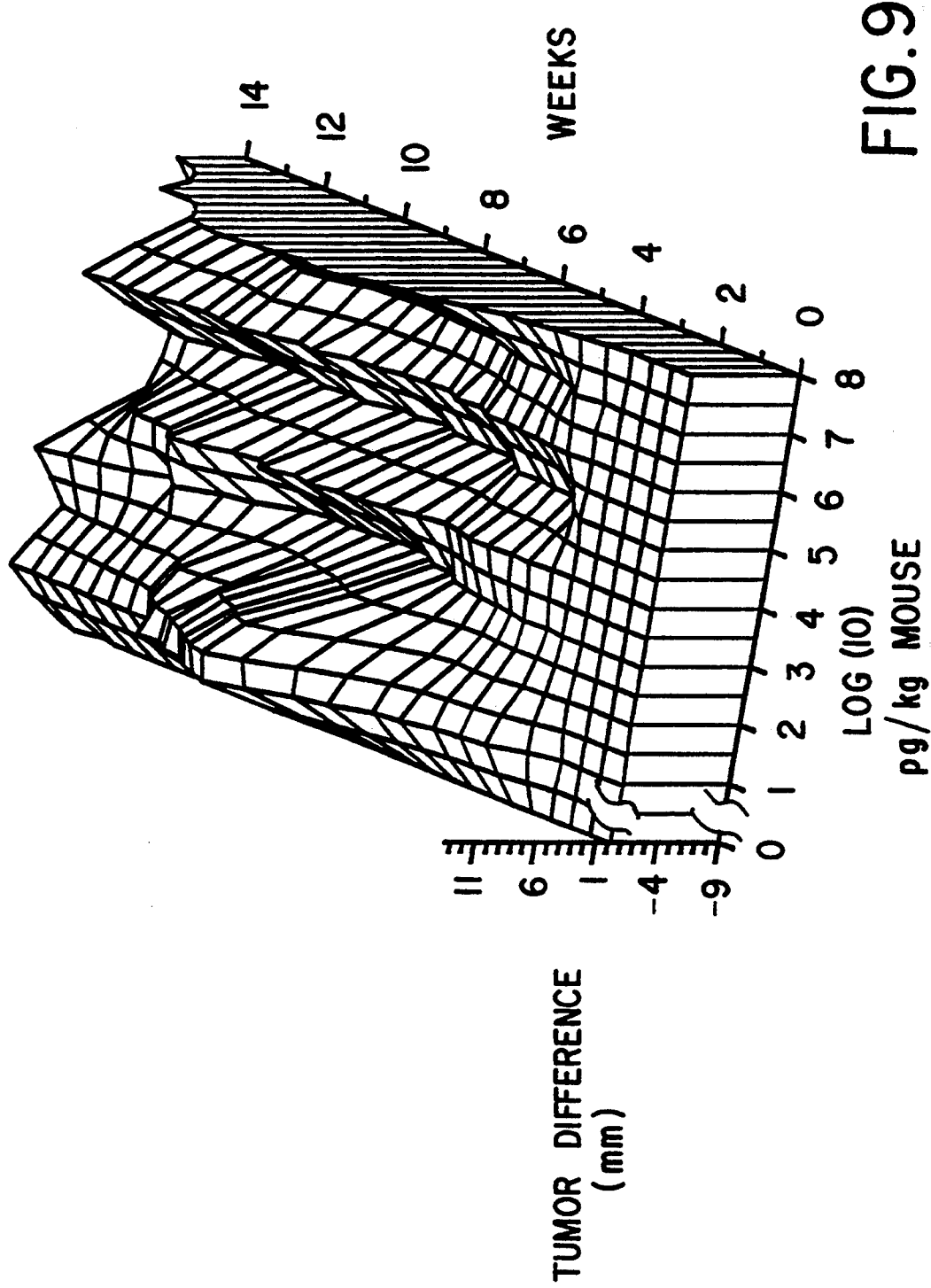
FIG. 9 illustrates the difference in average tumor development between mice receiving the combined therapy of FIG. 8 and the mice receiving the therapy of FIG. 7, i.e., the net effect of 1 ng vitaletheine V$_4$/kg mouse in modulating tumor development at differing concentrations of β-alethine after the response to β-alethine alone is subtracted.
Figure 10:
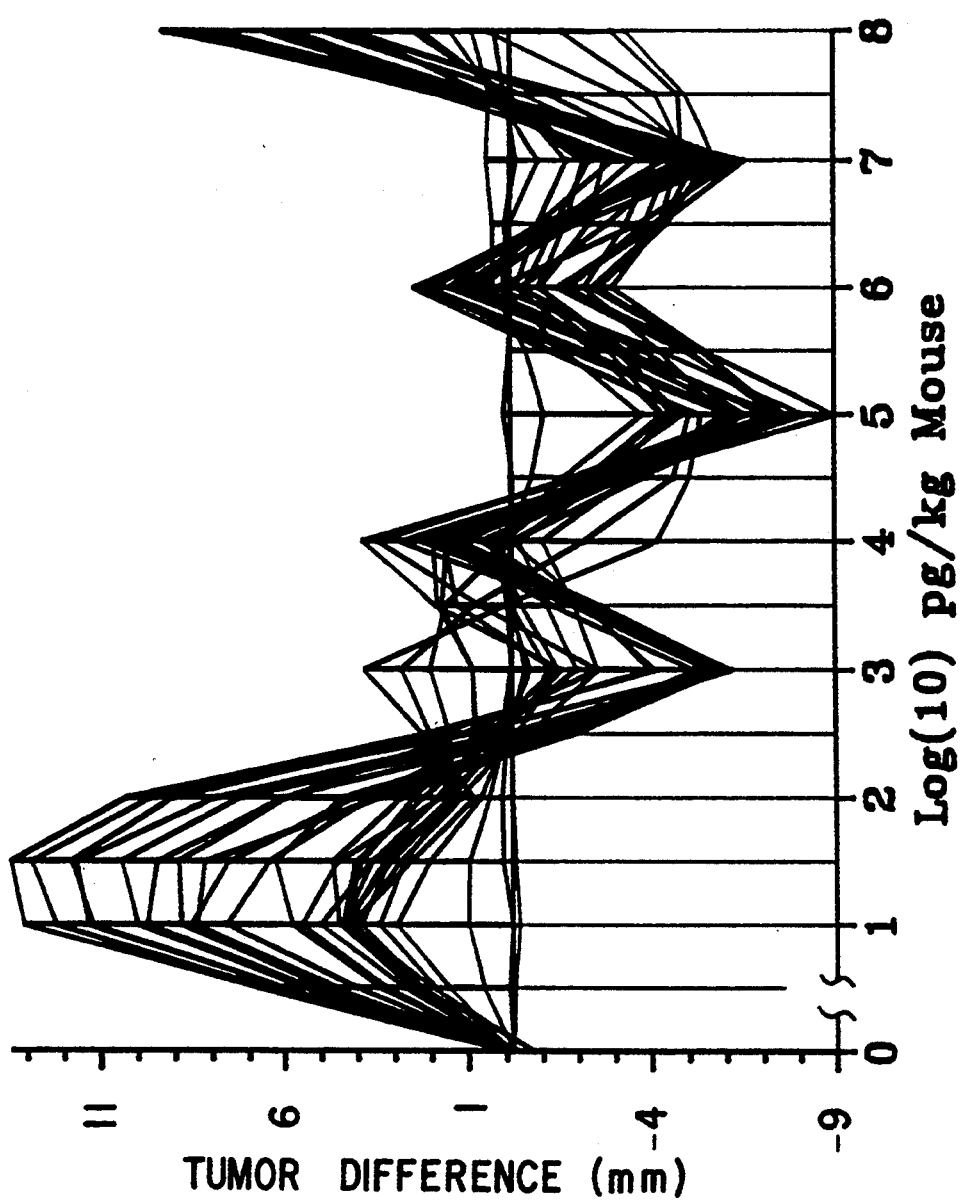
FIG. 10 (a counterclockwise rotation of FIG. 9) illustrates β-alethine concentrations optimizing the antitumor activity of 1 ng vitaletheine V$_4$/kg mouse.
Figure 11:
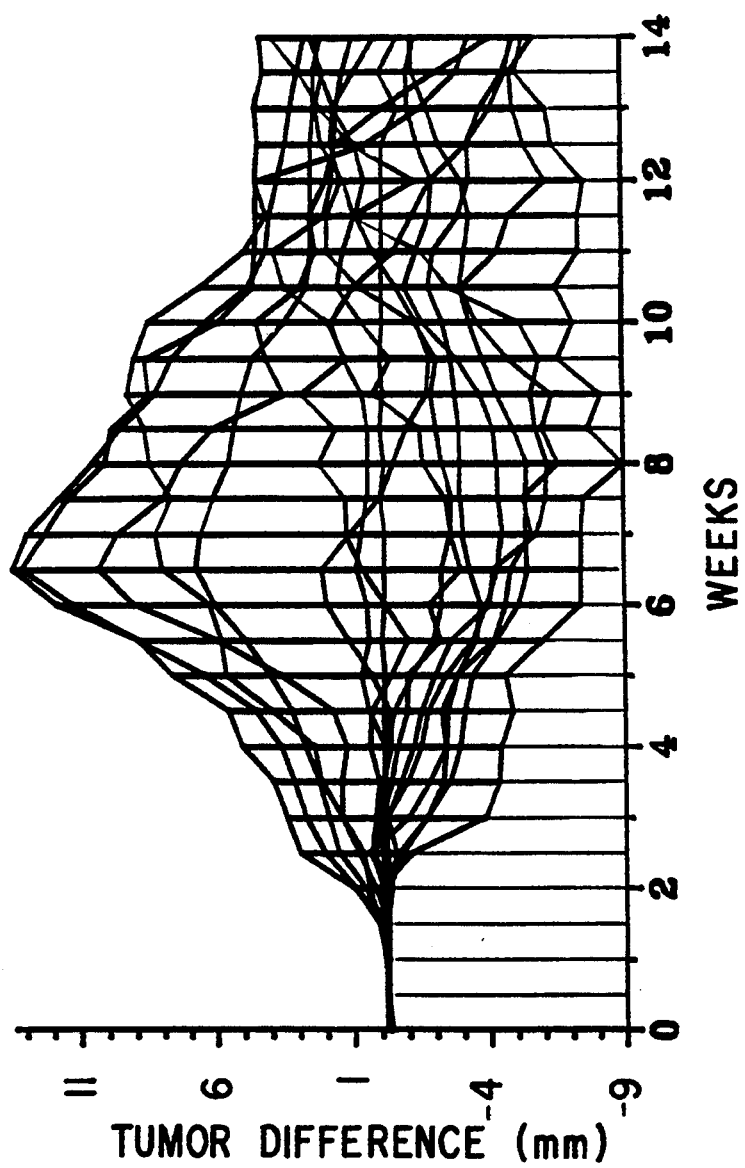
FIG. 11 (a clockwise rotation of FIG. 9) illustrates the net effect 1 ng vitaletheine V$_4$/kg mouse in preventing the development of tumor in mice receiving differing concentrations of β-alethine.
Figure 12:
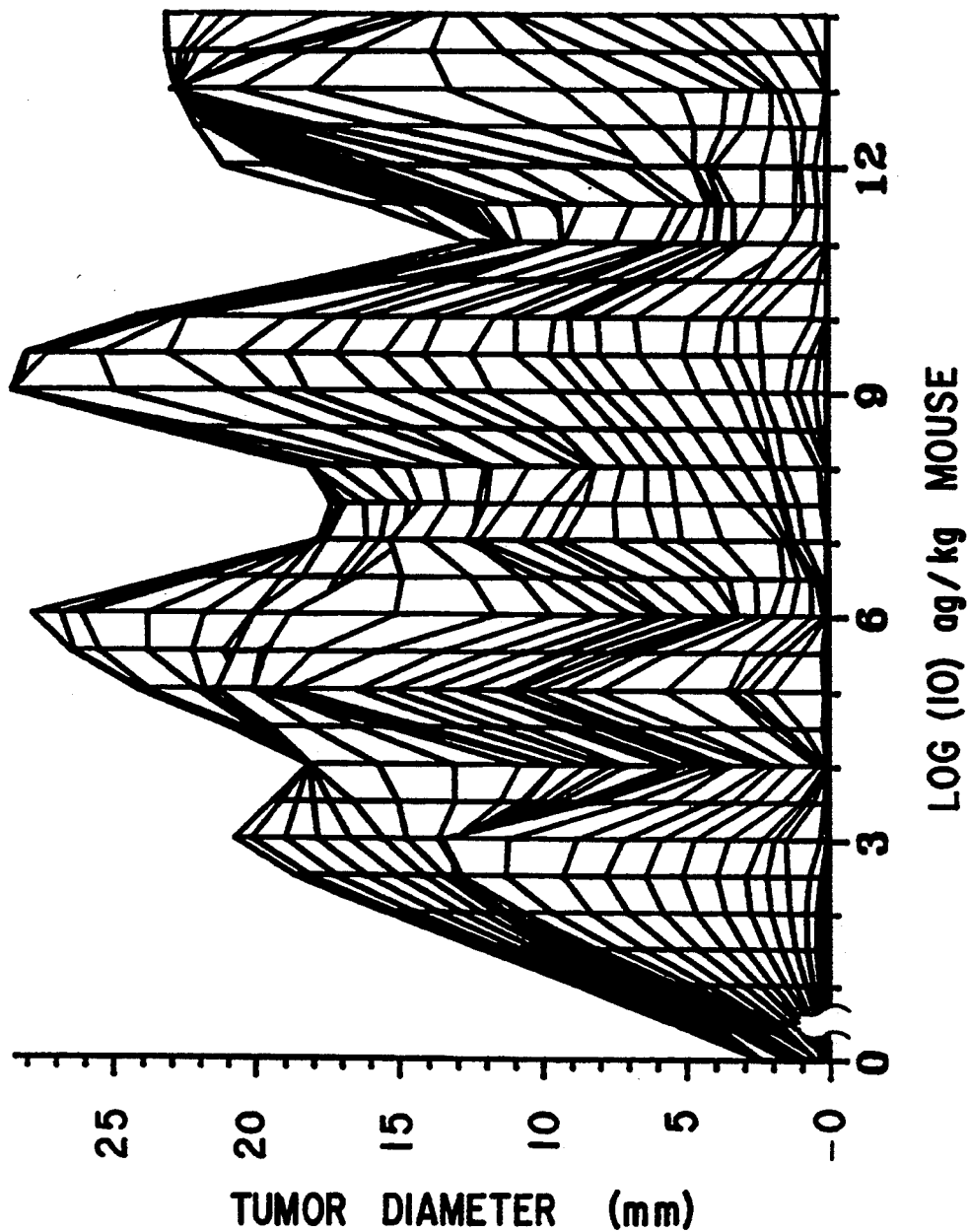
FIG. 12 illustrates average tumor development in five mice pretreated with saline (0) and in five mice pretreated with one of twelve log$_{(10)}$ increments of vitaletheine V$_4$ concentrations (1 fg/kg mouse to 100 μg/kg mouse)
Figure 13:
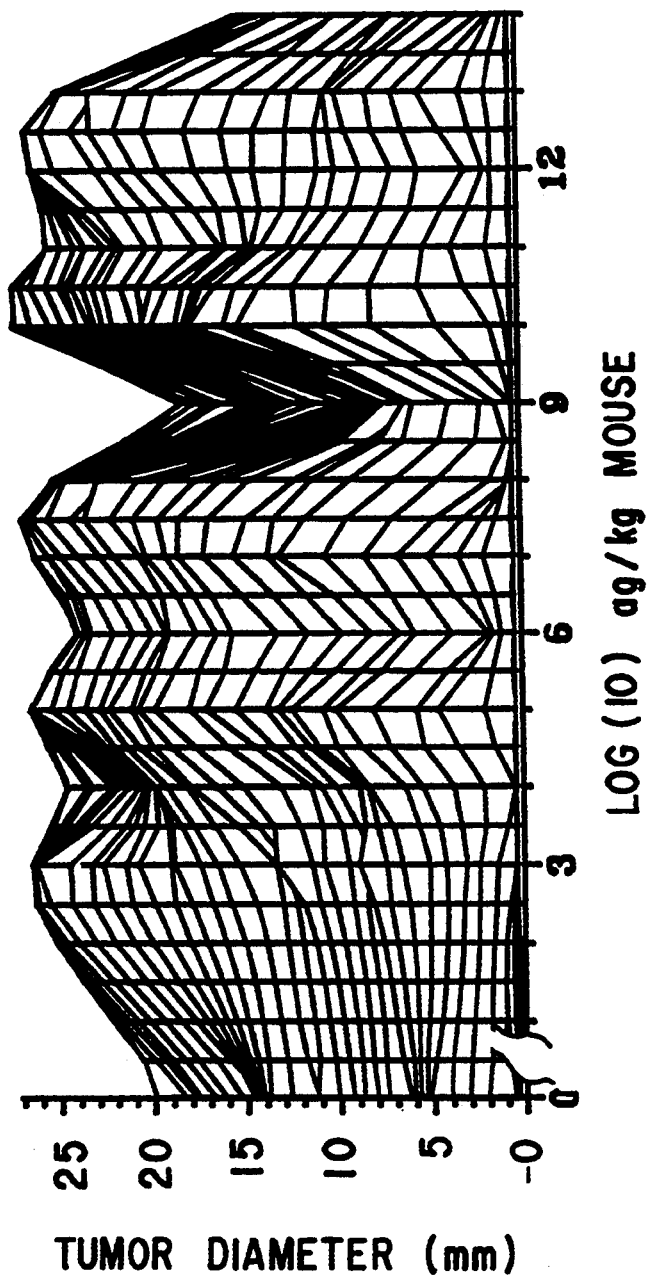
FIG. 13 illustrates average tumor development in five mice injected with a preparation in which the vitaletheine V$_4$ has been removed by filtration, plotted at the original or unfiltered concentration of vitaletheine V$_4$.
Figure 14:
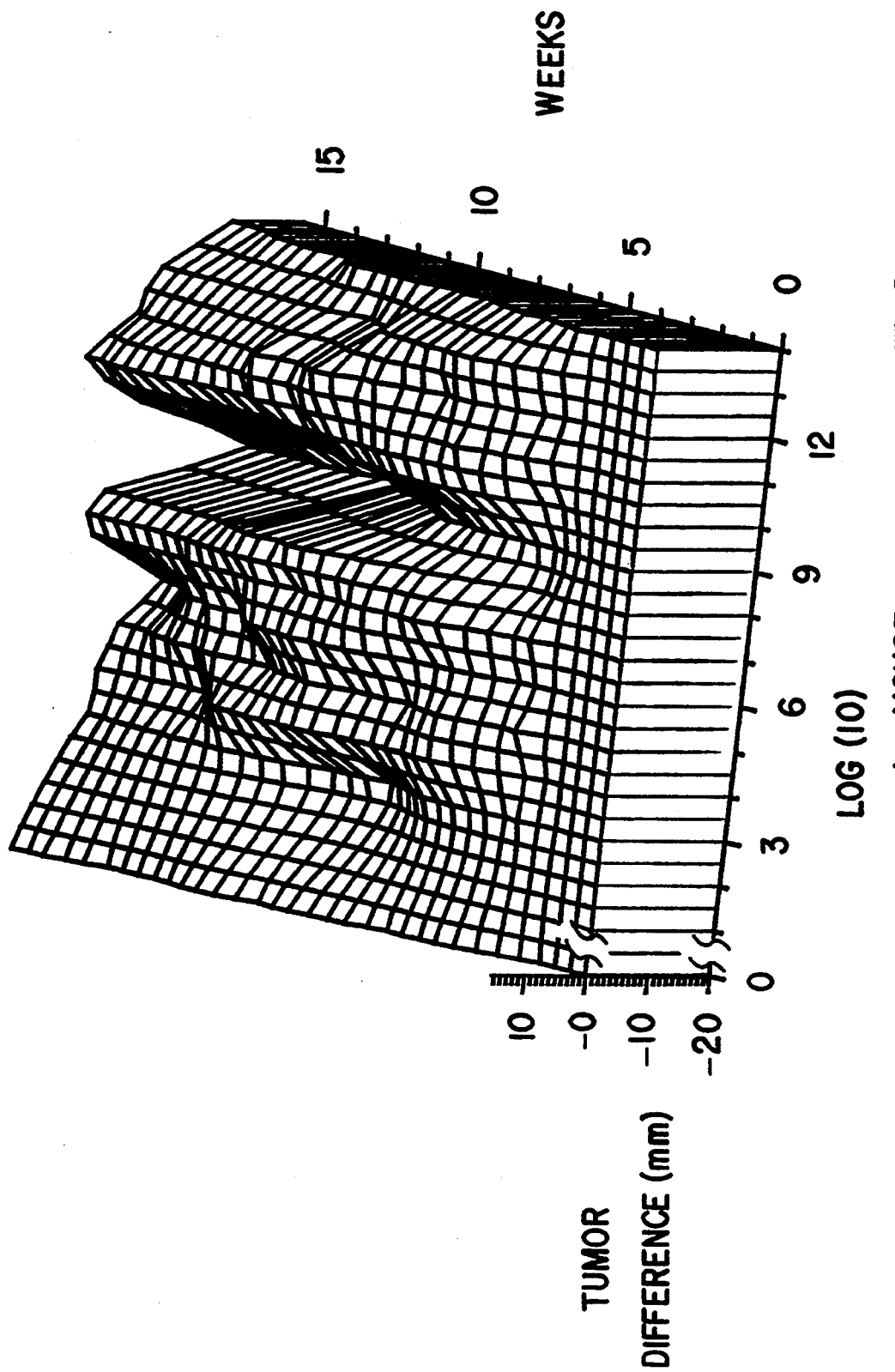
FIG. 14 illustrates the difference in average tumor development between mice treated with unfiltered vitaletheine V$_4$ and mice treated with a preparation in which the vitaletheine V$_4$ has been removed by filtration.
Figure 15:
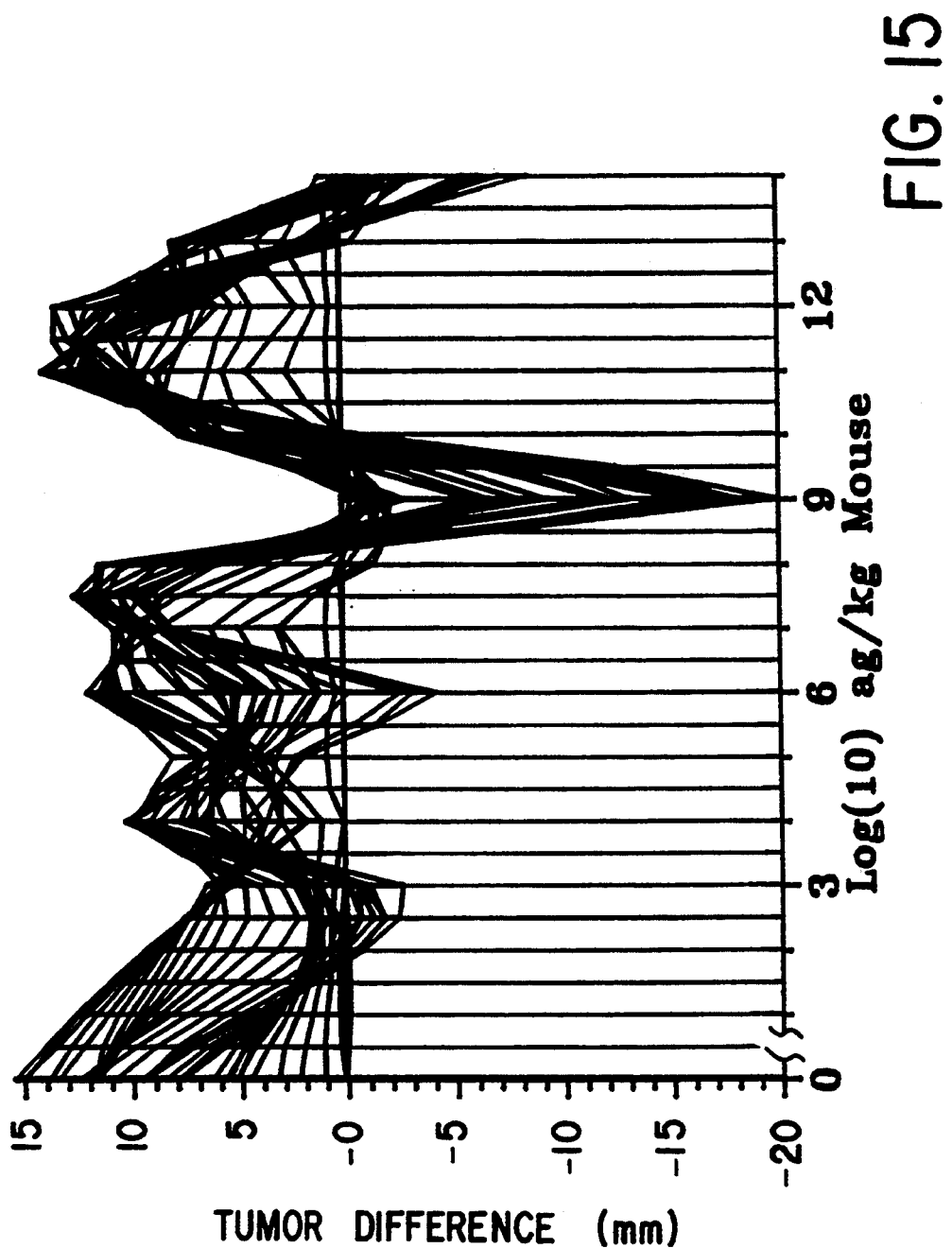
FIG. 15 (a counterclockwise rotation of FIG. 14) illustrates an optimal concentration of the filtrate in decreasing tumor burden (the filtered equivalent of 1 ng vitaletheine V$_4$/kg mouse), and the propensity for slower growth in older mice observed in FIG. 1.
Figure 16:
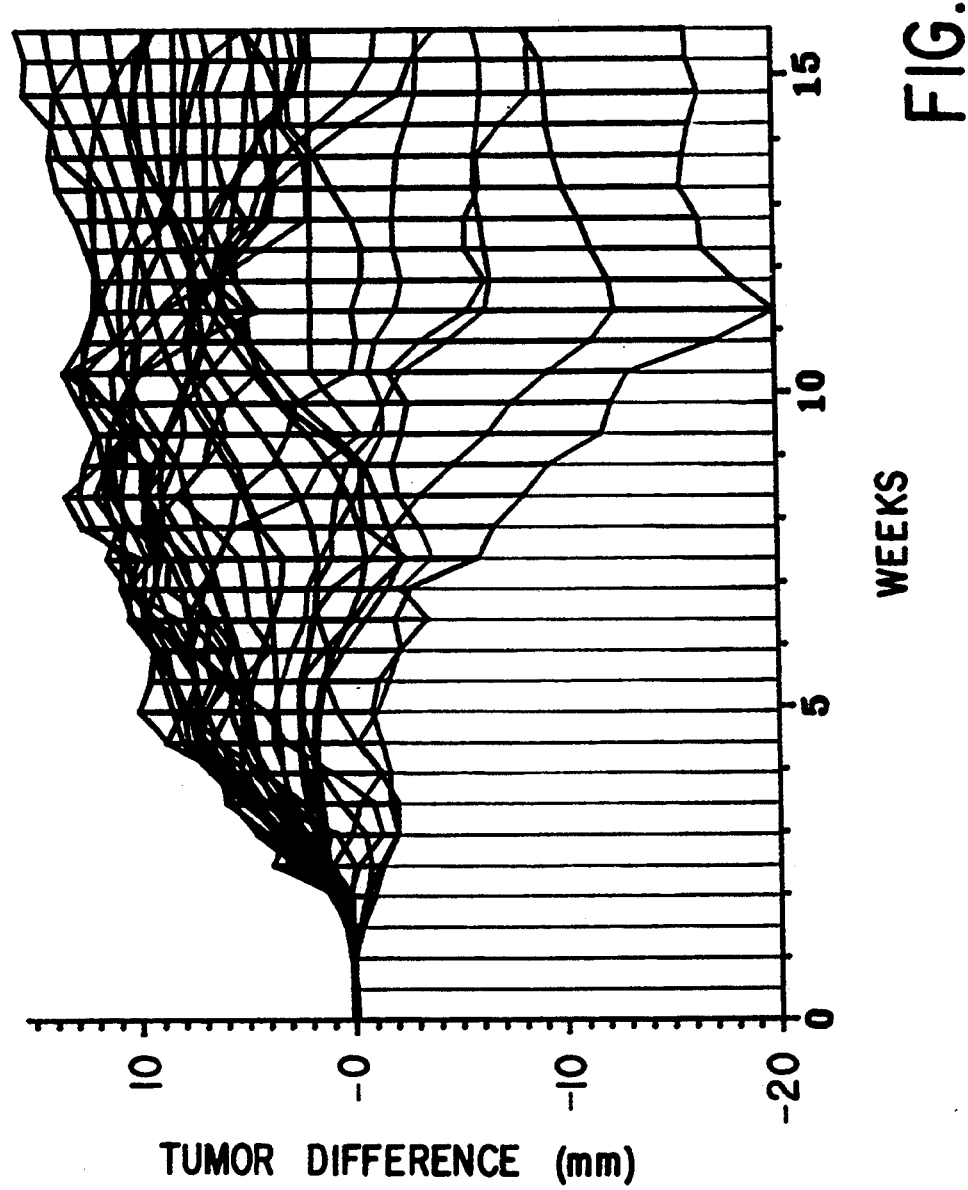
FIG. 16 (a clockwise rotation of FIG. 14) illustrates the net effect of filtering in improving the tumor-retardant properties of the vitaletheine V$_4$ preparation at differing concentrations of the original vitaletheine V$_4$ preparation.

The above considerations were necessary largely due to the propensity of compounds to polymerize when in the reduced or thiolate form. Indeed, when attempts were made to synthesize vitaletheine by irradiating high concentrations of its sulfenyl iodide with ultraviolet light, a polymer, a vitaletheine $V_4$, was produced, along with about 15% of the material in a dimer form (presumably vitalethine resulting from autooxidation and reaction of the thiolate with the sulfenyl iodide to form disulfide). Vitaletheine $V_4$ was not without therapeutic potential, for as an analogue of vitaletheine and vitalethine, it should inhibit degradation of the endogenous effectors. This potential was realized by combining vitaletheine $V_4$ and $\beta$-alethine therapies; note that the stimulation of tumor development by $\beta$-alethine (FIG. 7) was offset by the preparation vitaletheine $V_4$ (FIG. 8); and that the differences in these two surfaces (FIGS. 9, 10, and 11) define a therapeutic benefit of vitaletheine $V_4$, especially at 100 ng $\beta$-alethine/kg mouse. Unfortunately, vitaletheine $V_4$ as an analogue of vitaletheine and vitalethine also interfered with the function of the endogenous effectors (FIG. 12). Some of this interference was removed by filtering the vitaletheine $V_4$ preparation through a sterile Millex-GV filter (commercially available from Millipore Products Division, Bedford, Mass., U.S.A.) and in so doing removing a large portion of the interfering analogue (FIG. 13). The differences in these last two surfaces, FIGS. 12 and 13, indicated a therapeutic substance in the vitaletheine $V_4$ preparation permeable to the filter (FIGS. 14, 15, and 16). FIG. 15 also depicted dose-independent differences in the two surfaces which were explained readily by the age differences between the mice in these two experiments, the younger mice developing tumor more rapidly than the older mice, as in FIG. 1. From these observations and arguments it was obvious that vitaletheine had to be administered in a form that was either extremely dilute or stabilized to preclude polymerization. Since it was impractical to synthesize and characterize extremely dilute solutions of material, ways of presenting the cells or organisms with a stabilized form of vitaletheine were explored.

Figure 17:
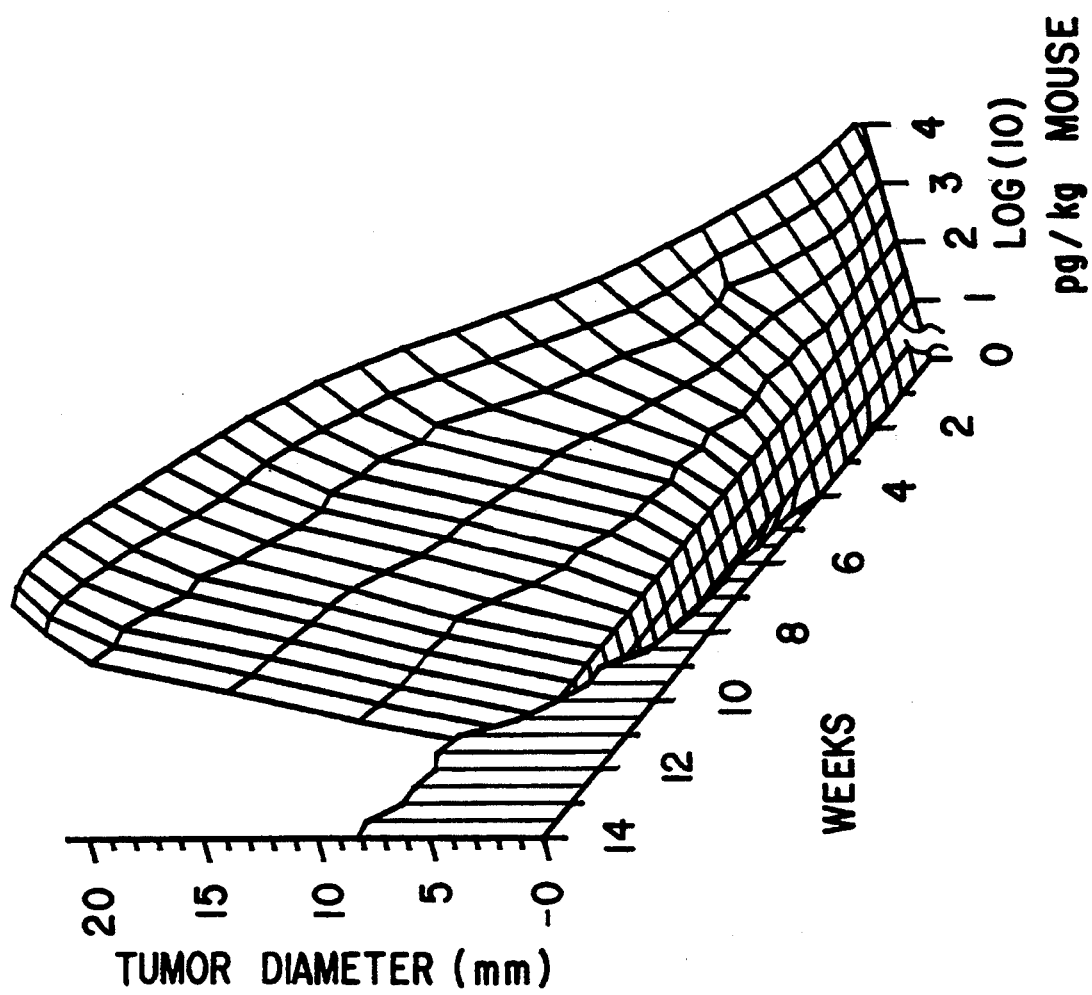
FIG. 17 illustrates average tumor development in five mice injected with one of three log$_{(10)}$ increments of vitalethine (100 pg to 10 ng vitalethine/kg mouse) relative to five mice injected with saline (0)
Figure 18:
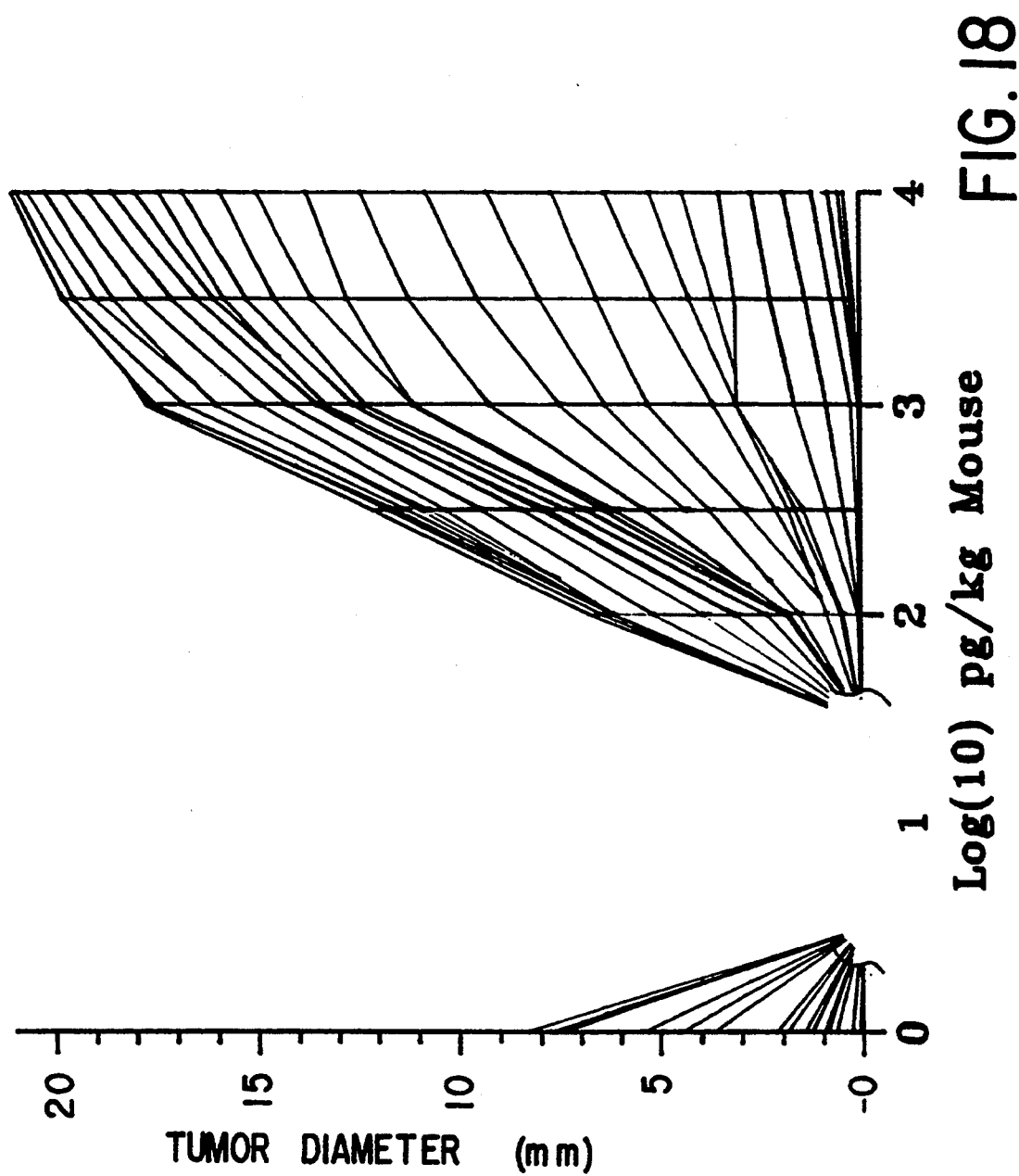
FIG. 18 (a clockwise rotation of FIG. 17) further illustrates the necessity for decreasing the concentration of injections of this preparation of vitalethine to 100 pg/kg mouseor less to obtain antitumor activity.
Figure 19:
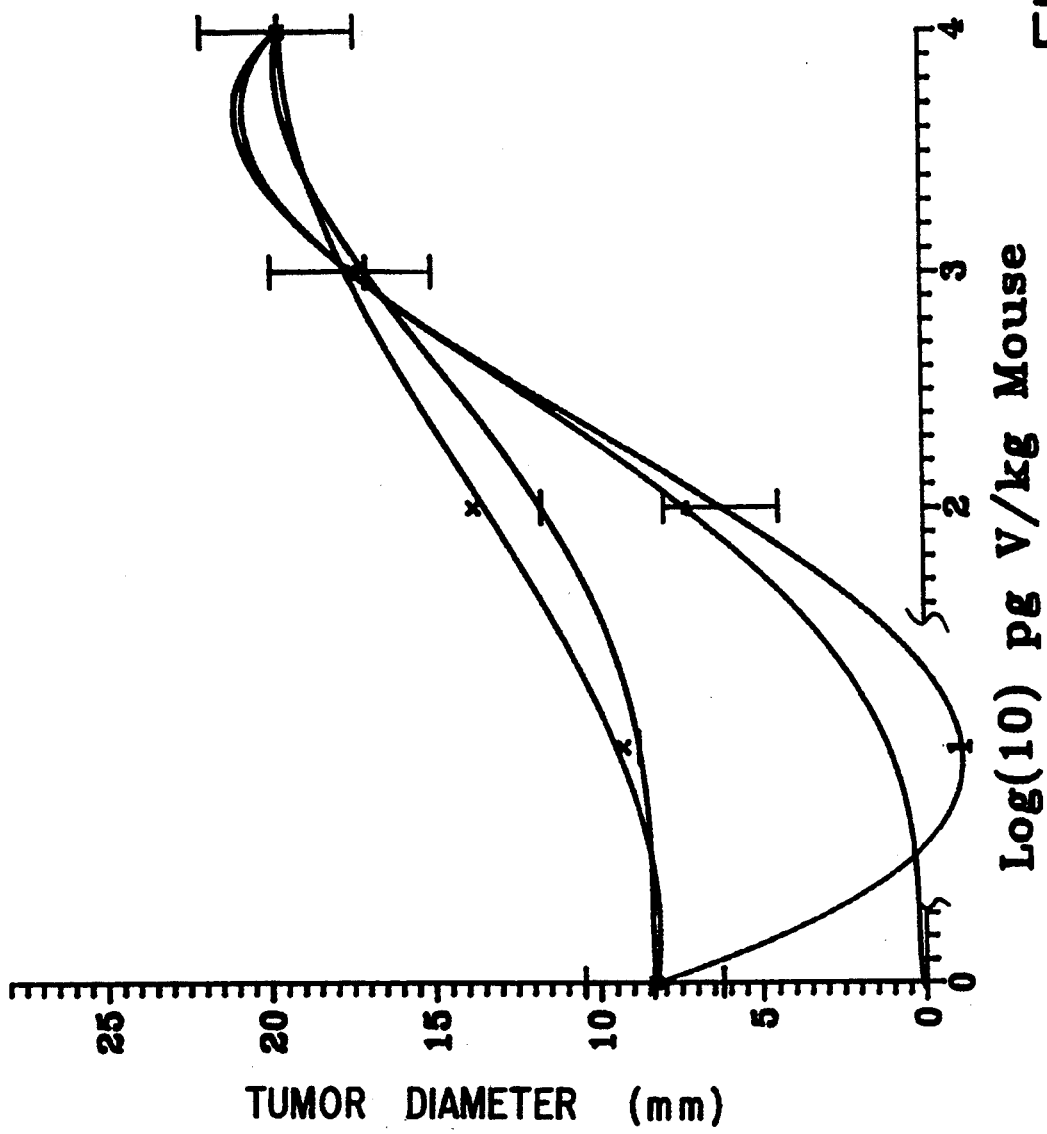
FIG. 19 further illustrates 1) an upper therapeutic limit for dosages of vitalethine according to the processes and methods of the invention (100 pg/kg mouse) in the treatment of Cloudman S-91 Melanoma in mice, using polynomial regression analysis and 3 degrees of freedom (bottom curve); 2) theoretical saturation curves for stimulation of tumor development with possible contaminants or metabolites (upper two curves); and 3) a theoretical saturation curve describing a therapeutic dose of vitalethine at low concentrations, followed by classical saturation kinetics of vitalethine being reduced to vitaletheine and at higher concentrations polymerizing to vitaletheine V$_4$ (polynomial regression analysis and 4 degrees of freedom, middle curve)
Figure 20:
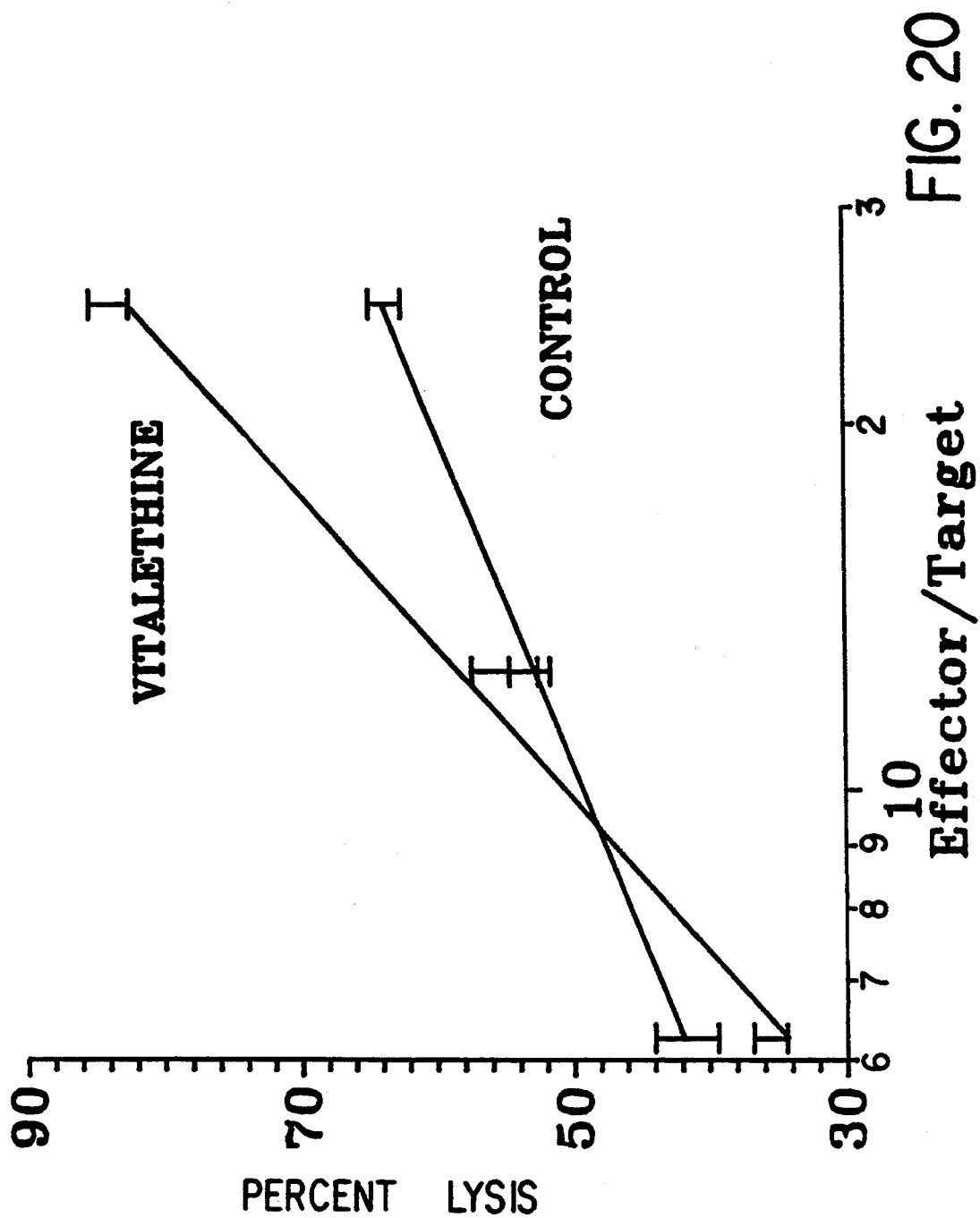
FIG. 20 illustrates a nine fold increase in the killing efficiency of a human leukocyte preparation containing NK (natural killer) cells in lysing 100% of human leukemic cells (K562) upon treatment of the cells with vitalethine for 6 days.

Problems with the synthesis and administration of vitaletheine were largely overcome by synthesis of vitalethine from the disulfide, $\beta$-alethine. Vitalethine, lacking the thiolate moiety, did not polymerize, was easily diluted, and when administered was presumed reduced by endogenous thiols and thiol-disulfide exchange mechanisms to vitaletheine. Furthermore, vitalethine was extremely potent in vivo, for unlike $\beta$-alethine and vitaletheine $V_4$, vitalethine diluted to tumor development levels less than control values; consequently an effective range of antineoplastic activity was indicated (FIG. 17). The therapeutic window for vitalethine was even more striking when surface and curve approximations were attempted (FIGS. 18 and 19). In vivo reduction and polymerization was indicated by neoplastic responses of the tumor at injection concentrations above 100 pg vitalethine/kg mouse (FIG. 18) which were very similar to the neoplastic responses to vitaletheine $V_4$ (FIG. 12), albeit the neoplastic responses to vitalethine occurred at much higher injection concentrations than those for vitaletheine $V_4$. The several explanations postulated for this observation include the following:

1) since a therapeutic response for vitalethine below 100 pg/kg mouse was strongly indicated by approximations using both a Kriging regional variable theory algorithm to analyze the entire study (FIGS. 17 and 18) and polynomial regression analysis of late points in the study (FIG. 19), the neoplastic responses to vitaletheine $V_4$, formed from vitalethine at injections concentrations less than 100 pg vitalethine/kg mouse, were offset by therapeutic responses to remaining vitalethine at these concentrations;
2) vitalethine itself interfered with vitaletheine effects when the concentration of the disulfide exceeds the reductive capacity of the target subcellular compartment;
3) the vitaletheine was formed intracellularly and was therefore partitioned within cellular and subcellular compartments in the mice so that higher concentrations were achieved without polymerization, than can be achieved with the reduced compound in free solution; and
4) the vitalethine is contaminated with growth promoting precursors and metabolites.

Regardless of the interpretation of the neoplastic response, neoplastic development was significantly less in mice treated with vitalethine at injection concentrations less than or equal to 100 pg/kg mouse (FIG. 19, bottom curve), especially when compared to theoretical saturation profiles for the stimulation of tumor development by vitaletheine $V_4$ (upper curves), and the theoretical development, in vivo, of vitaletheine $V_4$ from vitalethine via vitaletheine (middle curve). Combined therapies of vitalethine with other agents, and with inhibitors of vitalethine and vitaletheine degradation, especially vitaletheine $V_4$ and/or $\beta$-alethine are also contemplated.

Figure 21:
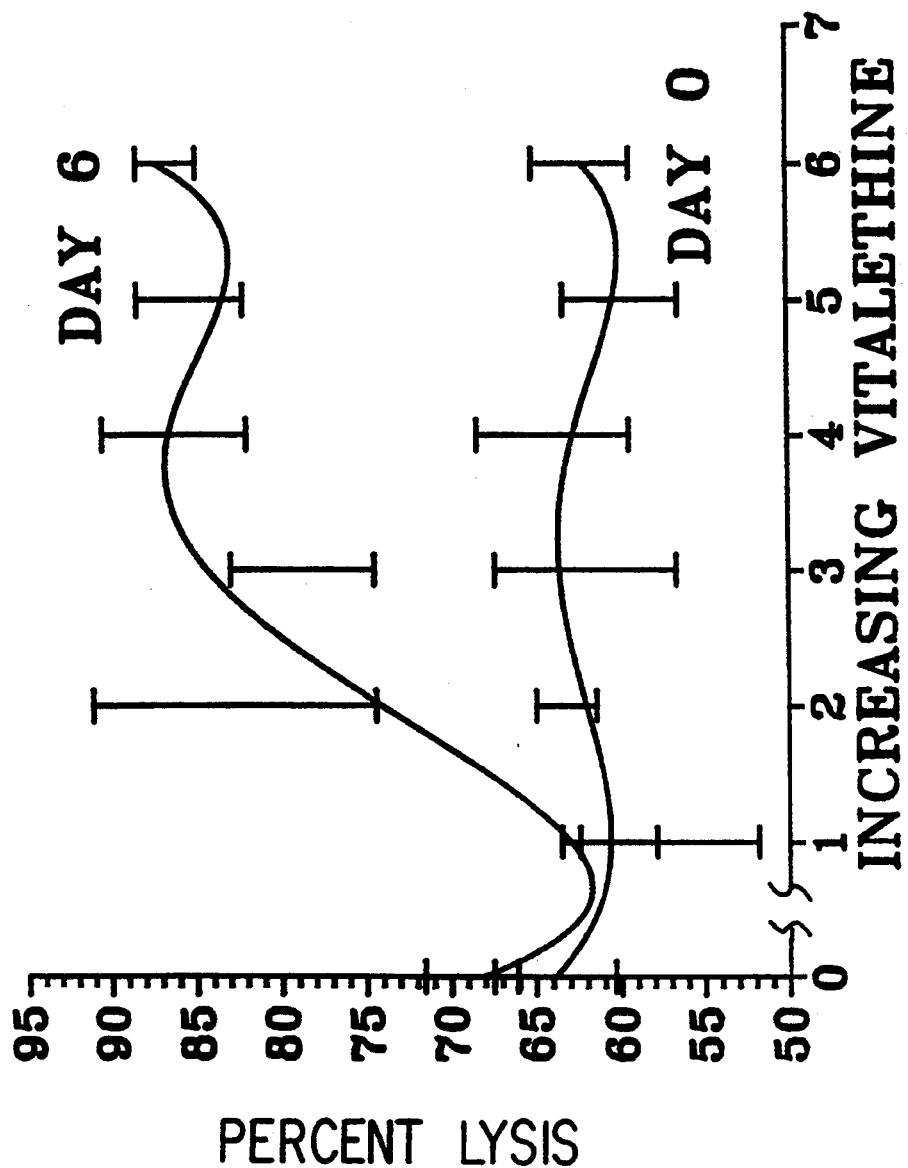
FIG. 21 illustrates that the stimulation of tumor cells lysis (K562) with the human leukocyte preparation containing NK cells is concentration-dependent, saturating or maximal at about 100 ag vitalethine/ml culture medium.

Example VIII: Vitalethine Stimulation, In Vitro, of the Lysis of Human Leukemic Cells (K562) Using a Preparation of Human NK (Natural Killer) Cells Glass non-adherent cells (GNAC's) were prepared as described in *J. Exp. Med.* 169: 99–113, 1989, incorporated herein by reference, using Ficoll-Hypaque gradients as described in *Scand. J. Clin. Lab. Invest.* 21(suppl. 97): 77–89, incorporated herein by reference, plating on glass, and passage through nylon wool columns as described in *J. Immunol.* 112: 420-423, incorporated herein by reference. The targeted K562 human leukemic cells (10,000) labeled with 51Cr (New England Nuclear Research Products, Dupont Company, Boston, Mass., U.S.A.) as described in *Arthritis Rheum.* 27: 1095-1100, incorporated herein by reference, were incubated in triplicate at each effector/target ratio (25, 12.5, or 6.25 times as many effector cells), or with 20% Triton X-100, to determine cytotoxicity of the effector cells (GNAC's), or maximum lysis of the target cells, respectively, during a 4 hour incubation. Cytotoxicity of the GNAC's was determined initially and after 6 days of exposure to 1, 10, $10^2$, $10^3$, $10^4$, $10^5$, $10^6$ ag vitalethine/ml culture (1 through 7 in FIG. 21).

Example IX: Influence of Metal Cations on Deblocking Reactions

A. The procedure in Example IIA was followed, except that magnesium or calcium ions were substituted for zinc ions in maintaining the pH of the reaction. The use of calcium or zinc cations resulted in benzyl derivatives of vitalethine (FIG. 22), whereas the use of magnesium salts in this procedure resulted in a cleavage of the N,N'-bis-carbobenzoxy-blocked beta-alethine (benzyl—V—S—S—V—benzyl) at the benzyl ester bond, and the recovery of the corresponding cyclic urethane of Formula IIf. The production of this cyclic urethane in the presence of magnesium ions was confirmed by IR analysis (unillustrated data), and by NMR analysis of the product of an intramolecular condensation of the two cyclic urethane moieties in $D_2O$. These reactions are though to proceed according to the following mechanisms:

NS-1 myeloma cells (ATCC TIB 18, P3/NS1-Ag4-1) were employed as inoculant in the BALBc/J mice model; these cells were about 90% effective in establishing myelomas in mice according to the exemplified procedure, and the untreated myelomas were substantially fatal within about two weeks. The cells were grown for several passages (preferably one week) in a sterile environment consisting of RPMI 1640 (Whittaker M. A. Bioproducts, Walkersville, Md., U.S.A.) containing 10% fetal calf serum (Hyclone Laboratories, Logan, Utah, U.S.A.), 2 mM L-glutamine, 5,000 units of penicillin, and 5 mg streptomycin in 75 $cm^2$ polystyrene tissue-culture flasks (Corning Glassworks, Corning, N.Y., U.S.A.) in a humidified chamber at 37° C. and under 6% $CO_2$. To assure NS-1 propagation in vivo, it was essential to remove DMSO (the cryostatic agent dimethyl sulfoxide) through several medium changes and dilutions; this also served to maintain the cells in log-phase growth. Female (BALBc/J) mice were injected i.p. with $10^4$ cells in 0.1 ml of standard phosphate-buffered saline as soon as possible after weaning, transport, and indexing, as it has been found that the NS-1 cell line employed does not generally perform optimally in animals which are mature or which have equilibrated with their environment. The mice were maintained with Wayne Rodent Blox (Wayne Research Animal Diets, Chicago, Ill., U.S.A.) ad. lib. and tap water. Concentrations of the benzyl derivative of vitaletheine based upon the average body weight of each group of mice were injected i.p. in 0.1 ml sterile physiological saline starting the second day after tumor inoculation, and continuing every Monday, Wednesday, and Friday throughout the study. Weights of tumor-inoculated, compound-treated mice were significantly lower when treated with certain

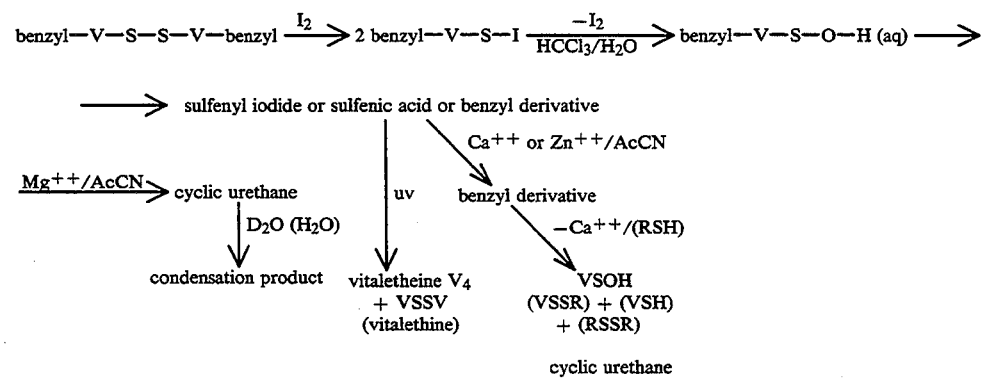

Intracellular concentrations of $Mg^{++}$ are mM, and $Ca^{++}$ concentrations are known to range from less than micromolar within the resting cell to over mM in the plasma. In vivo, activities of the benzyl derivative and vitalethine were comparable as illustrated by FIGS. 22 and 23, and 17, 18, and 19, respectively.

Example X: Calcium Salt of Benzyl Derivative Treats NS-1 Myeloma

Figure 22:
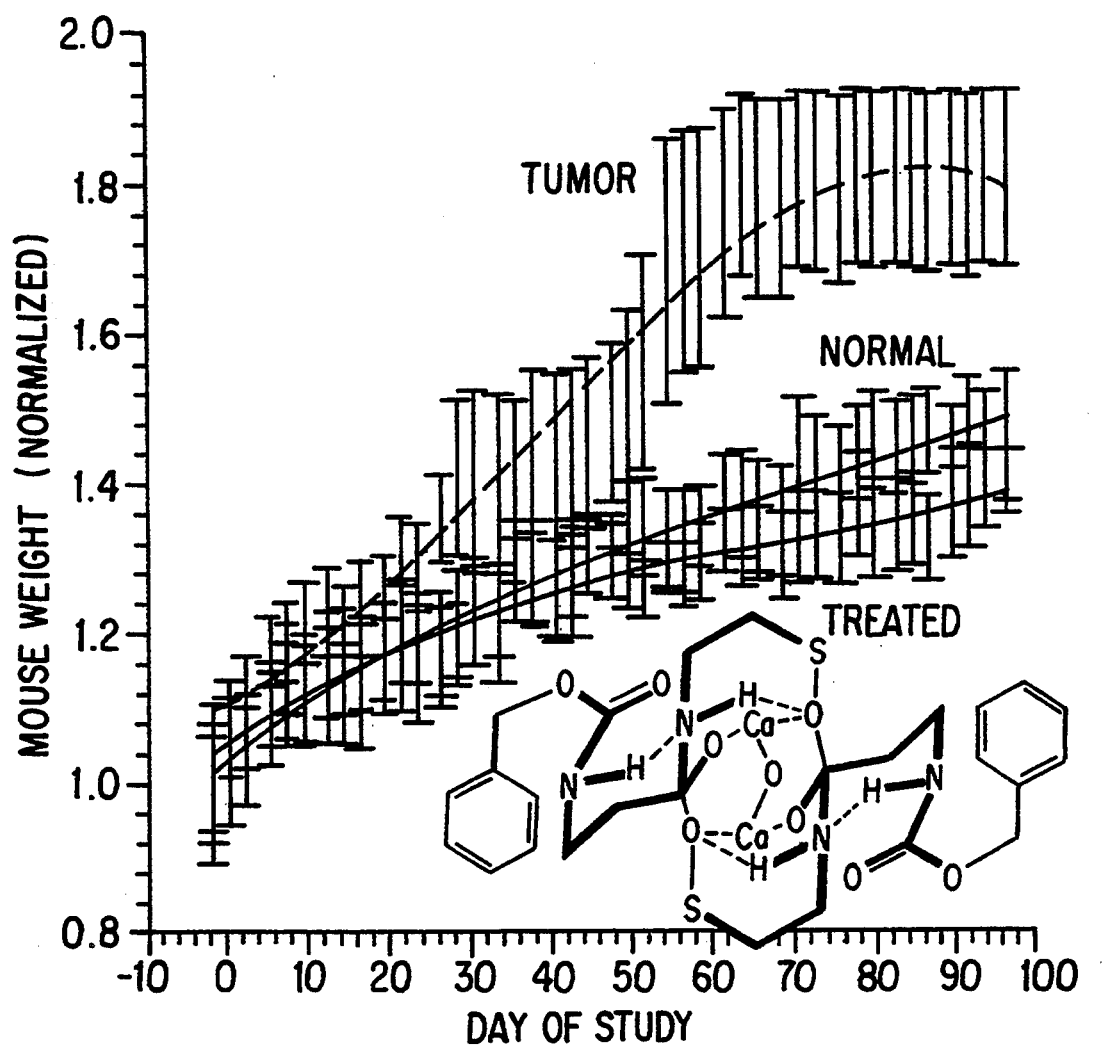
FIG. 22 illustrates weight increases reflecting tumor development in mice inoculated with NS-1 myeloma (top curve) relative to normal development of mice (middle curve), and to mice inoculated with tumor and treated with the calcium salt of the benzyl derivative (lower curve) according to Example IIa, IX, and X. Bars are standard error of the mean.
Figure 23:
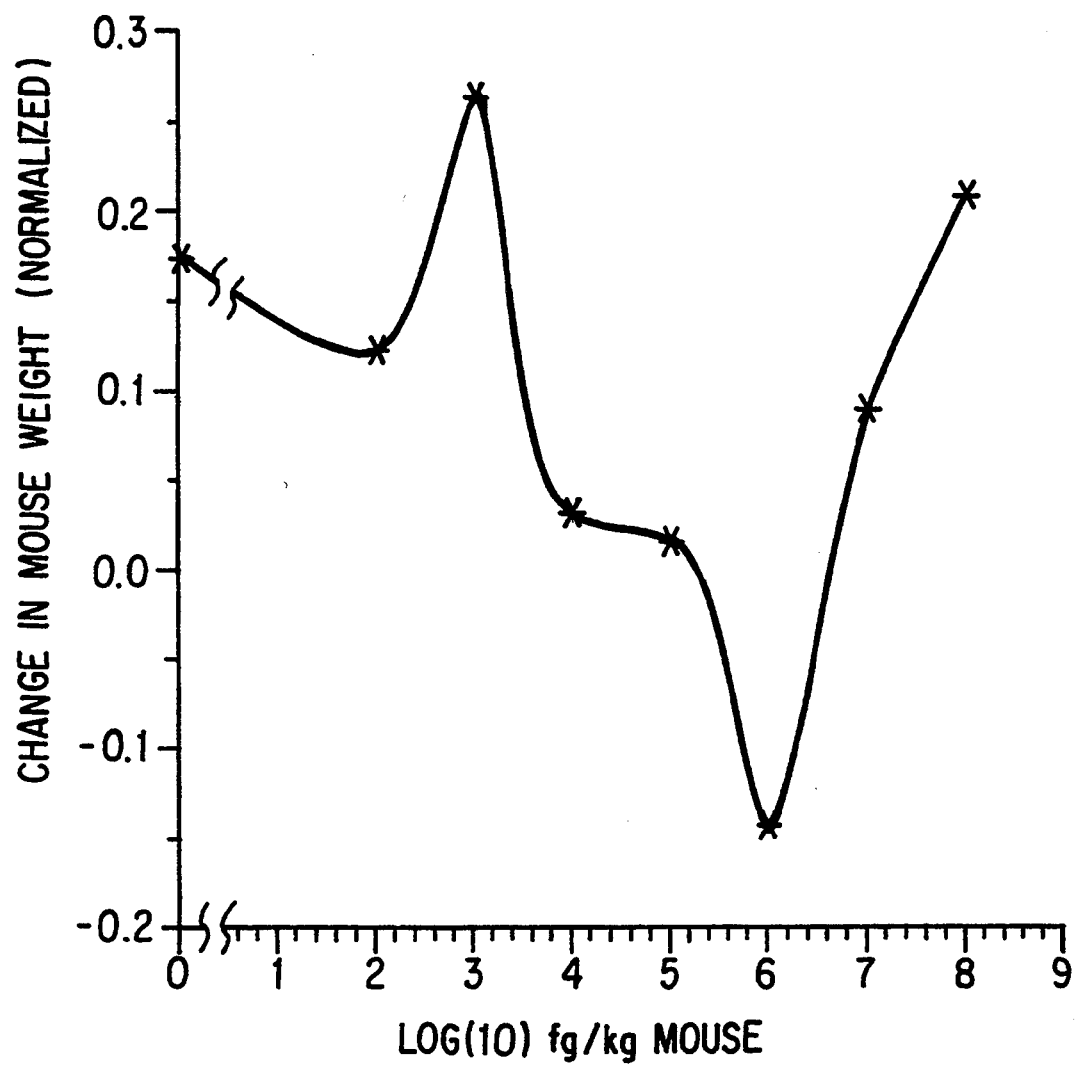
FIG. 23 illustrates the concentration-dependency of the response in FIG. 22, and the lack of tumor development observed at 100 pg benzyl derivative/kg mouse.

Instead of the direct measurement of the tumor diameter as in the melanoma model (FIG. 1), myeloma development was estimated by an increase in the weights of mice (reflecting ascites and solid tumor formation) relative to saline- and compound-injected controls. Groups were normalized to the average weight of each group at the start of the study, and bars are standard error of the mean.

concentrations of the benzyl derivatives (lower curve) compared to tumor-inoculated controls injected with saline (carrier) only (upper curve), and approximated those of saline-injected mice not challenged with tumor (middle curve) (FIG. 22). The weight differences between drug-treated, tumor-inoculated mice and their corresponding drug-treated controls not challenged with tumor were dependent upon the concentration of the benzyl derivative (FIG. 23).

What is claimed is:

1. A method for treating neoplasia comprising administering to an afflicted mammal an effective amount for treating neoplasia of vitalethine or a physiologically-compatible salt or tautomer thereof.

2. A method for treating neoplasia comprising administering to an afflicted mammal an effective amount for treating neoplasia of vitaletheine or a physiologically-compatible salt or tautomer thereof.

* * * * *